US007718382B2

(12) United States Patent
Coull et al.

(10) Patent No.: US 7,718,382 B2
(45) Date of Patent: May 18, 2010

(54) METHOD FOR IDENTIFYING COMPOUNDS FOR TREATMENT OF PAIN

(75) Inventors: Jeffrey A. M. Coull, Toronto (CA); Yves De Koninck, Ste-Foy (CA)

(73) Assignee: Universite Laval, Quebec, Quebec (CA)

( * ) Notice: Subject to any disclaimer, the term of this patent is extended or adjusted under 35 U.S.C. 154(b) by 588 days.

(21) Appl. No.: 11/596,087

(22) PCT Filed: May 13, 2005

(86) PCT No.: PCT/CA2005/000738

§ 371 (c)(1), (2), (4) Date: Nov. 9, 2006

(87) PCT Pub. No.: WO2005/110490

PCT Pub. Date: Nov. 24, 2005

(65) Prior Publication Data

US 2008/0260718 A1 Oct. 23, 2008

Related U.S. Application Data

(60) Provisional application No. 60/627,174, filed on Nov. 15, 2004.

(30) Foreign Application Priority Data

May 14, 2004 (WO) ............... PCT/CA2004/000726

(51) Int. Cl.
*G01N 33/53* (2006.01)
*G01N 33/567* (2006.01)

(52) U.S. Cl. ........................ 435/7.2; 435/7.1; 435/7.21; 436/501; 424/9.1; 514/2

(58) Field of Classification Search ....................... None
See application file for complete search history.

(56) References Cited

U.S. PATENT DOCUMENTS

| | | | | |
|---|---|---|---|---|
| 4,806,463 | A | 2/1989 | Goodchild et al. | |
| 5,004,810 | A | 4/1991 | Draper | |
| 5,034,506 | A | 7/1991 | Summerton et al. | |
| 5,087,617 | A | 2/1992 | Smith | |
| 5,098,890 | A | 3/1992 | Gewirtz et al. | |
| 5,135,917 | A | 8/1992 | Burch | |
| 5,166,195 | A | 11/1992 | Ecker | |
| 5,194,428 | A | 3/1993 | Agrawal et al. | |
| 5,264,423 | A | 11/1993 | Cohen et al. | |
| 5,276,019 | A | 1/1994 | Cohen et al. | |
| 5,286,717 | A | 2/1994 | Cohen et al. | |
| 5,474,921 | A * | 12/1995 | Koblan et al. | 435/196 |
| 5,539,082 | A | 7/1996 | Nielsen et al. | |
| 5,932,435 | A | 8/1999 | Atkins et al. | |
| 2002/0028779 | A1 | 3/2002 | High et al. | |
| 2002/0132788 | A1 | 9/2002 | Lewis et al. | |
| 2002/0173478 | A1 | 11/2002 | Gewirtz | |

FOREIGN PATENT DOCUMENTS

| | | | |
|---|---|---|---|
| DE | 3325506 | A1 | 1/1985 |
| WO | WO 93/00909 | | 1/1993 |
| WO | 95/21611 | A2 | 8/1995 |
| WO | WO 01/85151 | | 11/2001 |
| WO | WO 02/102232 | | 12/2002 |
| WO | WO 2004/032870 | | 4/2004 |

OTHER PUBLICATIONS

Malmberg et al. (1997). Preserved Acute Pain and Reduced Neuropathic Pain in Mice Lacking PKC-gamma. Science. 278:279-283.*

Lee et al. 2002. "Cdk4 and $p27^{Kip1}$ play a role in PLC-γ1-mediated mitogenic signaling pathway of 18 kDa FGF-2 in corneal endothelial cells." *Mol. Vis.* 8:17-25.

Monick et al. 1999. "A Phosphatidylcholine-Specific Phospholipase C Regulates Activation of p42/44 Mitogen-Activated Protein Kinases in Lipolysaccharide-stimulated Human Alveolar Macrophages." *J. Immunol.* 162:3005-3012.

Maragoudakis et al. 1993. "Basement membrane biosynthesis as a target for developing inhibitors of angiogenesis with anti-tumor properties." *Kidney Int.*, 43(1):147-150.

Schutze et al. 1992. "TNF Activates NF-kB by Phosphatidylcholine-Specific Phospholipase C-Induced 'Acidic' Sphingomyelin Breakdown." *Cell.* 71:765-776.

Muller-Decker, K. 1989. "Interruption of TPA-Induced Signals by an Antiviral and Antitumoral Xanthate Compound: Inhibition of a Phospholipase C-Type Reaction." *Biochem. Biophys. Res. Commun.* 162:198-205.

Sauer et al. 1984. "DNA and RNA virus species are inhibited by xanthates, a class of antiviral compounds with unique properties." *Proc. Natl. Acad. Sci. USA.* 81:3263-3267.

Carpenter et al. 1999. "Phospholipase C-γ as a Signal-Transducing Element." *Experimental Cell Research.* 253:15-24.

(Continued)

*Primary Examiner*—Christine J Saoud
*Assistant Examiner*—Jon M Lockard
(74) *Attorney, Agent, or Firm*—Ladas & Parry LLP

(57) ABSTRACT

The present invention provides methods of preventing and treating pain, by modulating, e.g. inhibiting, the activity, function and/or expression of a $PLC_γ$ in a subject. The invention further relates to methods of identifying agents capable of modulating the activity and/or expression of a $PLC_γ$, or capable of modulating binding of a ligand or binding partner to a $PLC_γ$, and their use thereof for the prevention and/or treatment of pain. In a further aspect, the invention provides methods for the diagnosis and prognostication of pain by determining whether there is modulation of activity and/or expression of a $PLC_γ$ relative to a corresponding control.

13 Claims, 10 Drawing Sheets

OTHER PUBLICATIONS

Noh et al. 1998. "Expression of Phospholipase C-γ1 and its Transcriptional Regulators in Breast Cancer Tissues." *Anticancer Research*. 18:2643-2648.
Shu et al. 2002. "Regulation of Phospholipase C-γ Activity by Glycosphingolipids." *J. Biol. Chem.* 277(21):18447-18453.
Mosconi et al. 1996. "Fixed-diameter polyethylene cuffs applied to the rat sciatic nerve induce a painful neuropathy: ultrastructural morphometric analysis of axonal alterations." *Pain*. 64:37-57.
Chaplan et al. 1994. "Quantitative assessment of tactile allodynia in the rat paw." *J. Neurosci. Methods*, 53:55-63.
Karim, et al. 2001. "Metabotropic Glutamate Receptor Subtypes 1 and 5 Are Activators of Extracellular Signal-Regulated Kinase Signaling Required for Inflammatory Pain in Mice." *J. Neurosci.* 3771-3779, vol. 21(11).
Galeotti et al. "The Phospholipase C-IP3 Pathway is Involved in Muscarinic Antinociception." *Neuropsychoopharmacol*, 2003, pp. 888-897. vol. 28.
Smith et al. 1999. "Involvement of phospholipid signal transduction pathways in morphine tolerance in mice." *Br. J. Pharmacol*, pp. 220-226, vol. 128.
Xie, et al. "Phospholipase C-γ1 Is Required for Calcium-induced Keratinocyte Differentiation." *J. Biol. Chem.* 1999. vol. 274(29). pp. 20421-20424.
Smith et al "Inhibition of Serum- and Ras-Stimulated DNA Synthesis by Antibodies to Phospholipase C." *Science*. 1990. vol. 247. pp. 1074-1077.
Buckley et al. "Identification of Phospholipase C-γ1 as a Mitogen-activated Protein Kinase Substrate." *J. Biol. Chem.* 2004. vol. 279(40). pp. 41807-41814.
Rhee. "Regulation of Phosphoinositide-Specific Phospholipase C." *Annu. Rev. Biochem*. 2001. vol. 70. pp. 281-312.
Melzack, et al. 1965. "Pain Mechanisms: A New Theory." *Science*. 150:971-979.
Woolf, et al. 2000. "Neuronal Plasticity: Increasing the Gain in Pain." *Science*. 288:1765-1769.
Kontinen, V.K., et al. 2001. "Electrophysiologic Evidence for Increased Endogenous GABAergic but Not Glycinergic Inhibitory Tone in the Rat Spinal Nerve Ligation Model of Neuropathy." *Anesthesiology*. 94:333-339.
Moore, K.A., et al. 2002. "Partial Peripheral Nerve Injury Promotes a Selective Loss of GABAergic Inhibition in the Superficial Dorsal Horn of the Spinal Cord." *J. Neurosci.* 22:6724-6731.
Somers, D.L., et al. 2002. "Dorsal horn synaptosomal content of aspartate, glutamate, glycine and GABA are differentially altered following chronic constriction injury to the rat sciatic nerve." *Neurosci Lett*. 323:171-174.
Polgar, E., et al. 2002. "GABA- and Glycine-Immunoreactivity in the Spinal Dorsal Horn of Rats with Peripheral Nerve Injury." *Soc. Neurosci. Abstr*. 28, 655.3.
Ebihara, S., et al. 1995. "Gramicidin-perforated patch recording: GABA response in mammalian neurons with intact intracellular chloride." *J. Physiol* 484 (pt 1), pp. 77-86.
Keller, A.F., et al. 2001. "Region-Specific Developmental Specialization of GABA-Glycine Cosynapses in Laminas I-II of the Rat Spinal Dorsal Horn." *J. Neurosci* 21:7871-7880.
Staley, K.J. et al. 1995. "Ionic Mechanisms of Neuronal Excitation by Inhibitory $GABA_A$ Receptors." *Science*. 269:977-981.
Coderre, T.J., et al. 1992. "The Contribution of Excitatory Amino Acids to Central Sensitization and Persistent Nociception after Formalin-induced Tissue Injury." *J. Neurosci.* 12:3665-3670.
Serpell, M.G. 2002. "Gabapentin in neuropathic pain syndromes: a randomised, double-blind, placebo-controlled trial." *Pain*. 99:557-566.
Rabben, T., et al. 1999. "Prolonged Analgesic Effect of Ketamine, an N-Methyl-D-Aspartate Receptor Inhibitor, in Patients with Chronic Pain." *J. Pharmacol. Exp. Ther*. 289:1060-1066.
Martin, T.J., et al. 2001. "Pharmacology of Opioid and Nonopioid Analgesics in Chronic Pain States." *J. Pharmacol. Exp. Ther.* 299:811-817.
Farber, N. B., et al. "Antiepileptic drugs and agents that inhibit voltage-gated sodium channels prevent NMDA antagonist neurotoxicity." 2002. *Mol. Psychiatry*. 7:726-733.
Mosconi, T., et al. 1996. "Fixed-diameter polyethylene cuffs applied to the rat sciatic nerve induce a painful neuropathy: ultrastructural morphometric analysis of axonal alterations." *Pain*. 64:37-57.
Coderre, T.J., et al. 1994. "The utility of excitatory amino acid (EAA) antagonists as analgesic agents. II. Assessment of the antinociceptive activity of combinations of competitive and non-competitive NMDA antagonists with agents acting at allosteric-glycine and polyamine receptor sites." *Pain*. 59:353-359.
Rivera, C., et al. 1999. "The $K^+$ /$Cl^-$ co-transporter KCC2 renders GABA hyperpolarizing during neuronal maturation." *Nature*. 397:251-255.
Prescott, S. A., et al. 2002. "Four cell types with distinctive membrane properties and morphologies in lamina I of the spinal dorsal horn of the adult rat." *J. Physiol*. 539:817-836.
Payne, J.A., et al. 1996. "Molecular Characterization of a Putative K-Cl Cotransporter in Rat Brain." *J. Biol. Chem*. 271:16245-16252.
Mount, D.B., et al. 1999. "Cloning and Characterization of KCC3 and KCC4, New Members of the Cation-Chloride Cotransporter Gene Family." *J. Biol. Chem*. 274:16355-16362.
Kelsch, W., et al. 2001. "Insulin-Like Growth Factor 1 and a Cytosolic Tyrosine Kinase Activate Chloride Outward Transport during Maturation of Hippocampal Neurons." *J Neurosci* 21:8339-8347.
Strange, K., et al. 2000. "Dependence of KCC2 K-Cl cotransporter activity on a conserved carboxy terminus tyrosine residue." *Am. J. Physiol Cell Physiol* 279:C860-C867.
Shen, M.R., et al. 2001. "The KCl cotransporter isoform KCC3 can play an important role in cell growth regulation." *Proc. Natl. Acad. Sci. USA*. 98:14714-14719.
Gulyas, A.I. et al. 2001. "The KCl cotransporter, KCC2, is highly expressed in the vicinity of excitatory synapses in the rat hippocampus." *Eur. J. Neurosci*. 13:2205-2217.
Payne, J.A. 1997. "Functional characterization of the neuronal-specific K-Cl cotransporter: implications for $[K^+]o$ regulation." *Am. J. Physiol*. 273:C1516-C1525.
Flatman, P.W., et al. 1996. "Role of protein kinases in regulating sheep erythrocyte K-Cl cotransport." *Am. J. Physiol* 271:C255-C263.
Howard, H.C., et al. 2002. "The K-Cl cotransporter KCC3 is mutant in a severe peripheral neuropathy associated with agenesis of the corpus callosum." *Nat. Genet*. 32:384-392.
Sung, K.W., et al. 2000. "Abnormal $GABA_A$ Receptor-Mediated Currents in Dorsal Root Ganglion Neurons Isolated from Na-K-2Cl Cotransporter Null Mice." *J. Neurosci*. 20:7531-7538.
Mainen, Z.F., et al. 1995. "A Model of Spike Initiation in Neocortical Pyramidal Neurons." *Neuron* 15:1427-1439.
Narikawa, K., et al. 2000. "In Vivo Patch-Clamp Analysis of IPSCs Evoked in Rat Substantia Gelatinosa Neurons by Cutaneous Mechanical Stimulation." *J. Neurophysiol*. 84:2171-2174.
Furue, H., et al. 1999. "Responsiveness of rat substantia gelatinosa neurons to mechanical but not thermal stimuli revealed by in vivo patch-clamp recording." *J. Physiol*. 521:529-535.
Ribeiro-da-Silva, A., et al. 1982. "Two Types of Synaptic Glomeruli and Their Distribution in Laminae I-III of the Rat Spinal Cord." *J. Comp. Neurol*. 209, 176-186.
Ribeiro-da-Silva, A. "Substantia Gelatinosa of Spinal Cord." *The Rat Nervous System*. Paxinos, G. (ed). pp. 47-59. Academic Press, Sydney, Australia, 1995.
Sik, A., et al. 2000. "Distribution of Chloride Channel-2-Immunoreactive Neuronal and Astrocytic Processes in the Hippocampus." *Neuroscience* 101, 51-65.
Gulyas, A.I., et al. 2001. "The KCl cotransporter, KCC2, is highly expressed in the vicinity of excitatory synapses in the rat hippocampus." *Eur. J. Neurosci*. 13, 2205-22 17.
Delpire, E., et al. 2002. "Human and Murine Phenotypes Associated with Defects in Cation-Chloride Cotransport." *Annu. Rev. Physiol*. 64:803-843.
Woo, N-S., et al. 2002. "Hyperexcitability and Epilepsy Associated with Disruption of the Mouse Neuronal-Specific K-Cl Cotransporter Gene." *Hippcampus* 12:258-268.
Rudomin, P., et al. 1999. "Presynaptic inhibition in the vertebrate spinal cord revisited." *Exp Brain Res*. 129:1-37.

Chaplan, S.R., et al. 1994. "Quantitative assessment of tactile allodynia in the rat paw." *J. Neuroscience Methods* 53:55-63.

Jarolimek et al. 1999. "A Furosemide-Sensitive $K^+$ $Cl^-$ Cotransporter Counteracts Intracellular $Cl^-$ Accumulation and Depletion in Cultured Rat Midbrain Neurons." *J. Neuroscience*. 19:4695-4704.

Kochuvelikakam, A.O., et al. "Role of Protein Kinase A in the Maintenance of Inflammatory Pain." *J. Neurosci*. 19, No. 6, 2181-2186, (1999).

Hua, X.Y., et al. 1999. "Inhibition of spinal protein kinase C reduces nerve injury-induced tactile allodynia in neuropathic rats." *Neuroscience Letters* 276. No. 2, 99-102.

Fang, L., et al. 2001. "Camk II Signalling in Central Sensitization in a Rat Model of Visceral Pain." *Database Biosis 'Online* 27, No. 2, 2163.

Coull, J. A. M. et al. 2003. "Trans-synaptic shift in anion gradient in spinal lamina I neurons as a mechanism of neuropathic pain." *Nature* (London). 424. No. 6951, 938-942.

De Plater, G.M. et al. 2001. "Venom From the Platypus, *Ornithorhynchus anatinus*, Induces a Calcium-Dependent Current in Cultured Dorsal Root Ganglion Cells." *J. Neurosci*. 85, No. 3, 1340-1345.

K. Tan-No, et al; "Intrathecal spermine and spermidine at high-doses induce antinociceptive effects in the mouse capsaicin test", Biogenic Amines, vol. 17, No. 4-6, pp. 313-320, 2003 (cannot find exact date) XP009120460, ISSN: 0168-8561.

Maria Ocana, et al; "Analgesic effects of centrally administered aminoglycoside antibiotics in mice", Neuroscience Letters, Limerick, IE, vol. 126, No. 1, May 13, 1991, pp. 67-70, XP024362849, ISSN: 0304-3940.

Amet Dogrul, et al; "Effects of Intrathecally Administered Aminoglycoside Antiobiotics, Calcium-Channel blockers, Nickel and Calcium on Acetic Acid-Induced Writhing Test in Mice", General Pharmacology, vol. 30, No. 4, Apr. 1998 (cannot find exact date), pp. 613-616, XP002538580, ISSN: 0306-3623.

W.A. Prado, et al; "Antinociceptive potency of aminoglycoside antibiotics and magnesium chloride: a comparative study on models of phasic and incisional pain in rats", Brazilian Journal of Medical and Biological Research, Ribeirao Preto, BR, vol. 35, No. 3, Mar. 1, 2002, pp. 395-403, XP009120234, ISSN: 0100-879X.

Ian C.B. Marshall, et al; "Activation of vanilloid receptor 1 by resiniferatoxin mobilizes calcium from inositol 1,4,5-trisphosphate-sensitive stores", British Journal of Pharmacology, vol. 138, No. 1, Jan. 2003 (cannot find exact date), pp. 172-176, XP002538581, ISSN: 0007-1188.

M. Narita, et al; Role of the Phosphatidylinositol-Specific Phospholipase C Pathway in Delta-Opioid Receptor-Mediated Antinociception in the Mouse Spinal Cord (2000), Neuroscience 99(2): 327-331.

European Search Report: PCT/CA2005000738, (Jul. 2009).

* cited by examiner

DNA sequence of human phospholipase C gamma 1 (PLCG1; SEQ ID NO: 1).
Coding sequence defined by positions 122-3997. Accession no. NM_002660.

```
   1 gagccgccgc cgggtcccgc tcgtctgccg cctcagcctc agccccaacc tcagccgccg
  61 ccgttgcgct tgctcccggg cggtcctggc ctgtgccgcc gccgccccca gcgtcggagc
 121 catggcgggc gccgcgtccc cttgcgccaa cggctgcggg cccggcgcgc cctcggacgc
 181 cgaggtgctg cacctctgcc gcagcctcga ggtgggcacc gtcatgactt tgttctactc
 241 caagaagtcg cagcgacccg agcggaagac cttccaggtc aagctggaga cgcgccagat
 301 cacgtggagc cggggcgccg acaagatcga gggggccatt gacattcgtg aaattaagga
 361 gatccgccca gggaagacct cacgggactt tgatcgctat caagaggacc cagctttccg
 421 gccggaccag tcacattgct ttgtcattct ctatggaatg gaatttcgcc tgaaaacgct
 481 gagcctgcaa gccacatctg aggatgaagt gaacatgtgg atcaagggct taacttggct
 541 gatggaggat acattgcagg cacccacacc cctgcagatt gagaggtggc tccggaagca
 601 gttttactca gtggatcgga atcgtgagga tcgtatatca gccaaggacc tgaagaacat
 661 gctgtcccag gtcaactacc gggtccccaa catgcgcttc ctccgagagc ggctgacgga
 721 cctggagcag cgcagcgggg acatcaccta cggccagttt gctcagctgt accgcagcct
 781 catgtacagc gcccagaaga cgatggacct cccctcttg gaagccagta ctctgagggc
 841 tggggagcgg ccggagcttt gccgagtgtc ccttcctgag ttccagcagt tccttcttga
 901 ctaccagggg gagctgtggg ctgttgatcg cctccaggtg caggagttca tgctcagctt
 961 cctccgagac cccttacgag agatcgagga gccatacttc ttcctggatg agtttgtcac
1021 cttcctgttc tccaaagaga acagtgtgtg gaactcgcag ctggatgcag tatgcccgga
1081 caccatgaac aaccctcttt cccactactg gatctcctcc tcgcacaaca cgtacctgac
1141 cggggaccag ttctccagtg agtcctcctt ggaagcctat gctcgctgcc tgcggatggg
1201 ctgtcgctgc attgagttgg actgctggga cggcccggat gggatgccag ttatttacca
1261 tgggcacacc cttaccacca agatcaagtt ctcagatgtc ctgcacacca tcaaggagca
1321 tgcctttgtg gcctcagagt acccagtcat cctgtccatt gaggaccact gcagcattgc
```

FIG. 2A

```
1381 ccagcagaga aacatggccc aatacttcaa gaaggtgctg ggggacacac tcctcaccaa
1441 gcccgtggag atctctgccg acgggctccc ctcacccaac cagcttaaga ggaagatcct
1501 catcaagcac aagaagctgg ctgagggcag tgcctacgag gaggtgccta catccatgat
1561 gtactctgag aacgacatca gcaactctat caagaatggc atcctctacc tggaggaccc
1621 tgtgaaccac gaatggtatc cccactactt tgttctgacc agcagcaaga tctactactc
1681 tgaggagacc agcagtgacc agggcaacga ggatgaggag gagcccaagg aggtcagcag
1741 cagcacagag ctgcactcca atgagaagtg gttccatggg aagctagggg cagggcgtga
1801 cgggcgtcac atcgctgagc gcctgcttac tgagtactgc atcgagaccg gagcccctga
1861 cggctccttc ctcgtgcgag agagtgagac cttcgtgggc gactacacgc tctctttctg
1921 gcggaacggg aaagtccagc actgccgtat ccactcccgg caagatgctg ggacccccaa
1981 gttcttcttg acagacaacc tcgtctttga ctccctctat gacctcatca cgcactacca
2041 gcaggtgccc ctgcgctgta atgagtttga gatgcgactt tcagagcctg tcccacagac
2101 caacgcccac gagagcaaag agtggtacca cgcgagcctg accagagcac aggctgagca
2161 catgctaatg cgcgtccctc gtgatggggc cttcctggtg cggaagcgga atgaacccaa
2221 ctcatatgcc atctctttcc gggctgaggg caagatcaag cattgccgtg tccagcaaga
2281 gggccagaca gtgatgctag ggaactcgga gttcgacagc cttgttgacc tcatcagcta
2341 ctatgagaaa cacccgctat accgcaagat gaagctgcgc tatcccatca acgaggaggc
2401 actggagaag attggcacag ctgagcctga ctacggggcc ctgtatgagg gacgcaaccc
2461 tggcttctat gtagaggcaa accctatgcc aactttcaag tgtgcagtca aagccctctt
2521 tgactacaag gcccagaggg aggacgagct gaccttcatc aagagcgcca tcatccagaa
2581 tgtggagaag caagagggag gctggtggcg aggggactac ggagggaaga agcagctgtg
2641 gttcccatca aactacgtgg aagagatggt caaccccgtg gccctggagc cggagaggga
2701 gcacttggac gagaacagcc ccctagggga cttgctgcgg ggggtcttgg atgtgccggc
2761 ttgtcagatt gccatccgtc ctgagggcaa gaacaaccgg ctcttcgtct tctccatcag
2821 catggcgtcg gtggcccact ggtccctgga tgttgctgcc gactcacagg aggagctgca
2881 ggactgggtg aaaaagatcc gtgaagtggc ccagacagca gacgccaggc tcactgaagg
2941 gaagataatg gaacggagga agaagattgc cctggagctc tctgaacttg tcgtctactg
```

FIG. 2B

```
3001 ccggcctgtt ccctttgatg aagagaagat tggcacagaa cgtgcttgct accgggacat
3061 gtcatccttc ccggaaacca aggctgagaa atacgtgaac aaggccaaag gcaagaagtt
3121 ccttcagtac aatcgactgc agctctcccg catctacccc aagggccagc gactggattc
3181 ctccaactac gatcctttgc ccatgtggat ctgtggcagt cagcttgtgg ccctcaactt
3241 ccagacccct gacaagccta tgcagatgaa ccaggccctc ttcatgacgg gcaggcactg
3301 tggctacgtg ctgcagccaa gcaccatgcg ggatgaggcc ttcgacccct ttgacaagag
3361 cagcctccgc gggctggagc catgtgccat ctctattgag gtgctggggg cccgacatct
3421 gccaaagaat ggccgaggca ttgtgtgtcc ttttgtggag attgaggtgg ctggagctga
3481 gtatgacagc accaagcaga agacagagtt tgtggtggac aatggactca accctgtatg
3541 gccagccaag cccttccact tccagatcag taaccctgaa tttgcctttc tgcgcttcgt
3601 ggtgtatgag gaagacatgt ttagtgacca gaatttcctg gctcaggcta ctttcccagt
3661 aaaaggcctg aagacaggat acagagcagt gcctttgaag aacaactaca gtgaggacct
3721 ggagttggcc tccctgctga tcaagattga cattttccct gccaagcagg agaatggtga
3781 cctcagtccc ttcagtggta cgtccctgcg ggagcggggc tcagatgcct caggccagct
3841 gtttcatggc cgagcccggg aaggctcctt tgaatcccgc taccagcagc cgtttgagga
3901 cttccgcatc tcccaggagc atctcgcaga ccattttgac agtcgagaac gaagggcccc
3961 aagaaggact cgggtcaatg gagacaaccg cctctagttg taccccagcc tcgttggaga
4021 gcagcaggtg ctgtgcgcct tgtagaatgc cgcgaactgg gttctttgga agcagccccc
4081 tgtggcggcc ttccgggtct cgcagcctga agcctggatt ccagcagtga atgctagaca
4141 gaaaccaagc cattaatgag atgttattac tgttttgggc ctccatgccc cagctctgga
4201 tgaaggcaaa aactgtactg tgtttcgcat taagcacaca catctggccc tgacttctgg
4261 agatggatcc ttccatcttg tggggccagg accatggccg aagccccttg gagagagagg
4321 ctgcctcagc cagtggcaca ggagactcca aggagctact gacattccta agagtggagg
4381 aggaggagga gccttgctgg gccagggaaa caaagtttac attgtcctgt agctttaaaa
4441 ccacagctgg gcagggtgag aagctagatg cccctgcagt ttggccctgg agccagggca
4501 gaggaatgta gggcctgcat ggagaagggt tctgccctgc ctgaggagga ggacacagca
4561 caagggcaca ttgcccatgg ctgggaacat gacccagcct gaaagataca ggggatcatg
```

FIG. 2C

```
4621 ttaaaaatag cagtattatt tttcgtctca atggtattgt aactaagtta tttactcctc
4681 ctgctcctca cccctgtagg gaaaccttgg agaggagagt ggcaggtggg ctgcctgctg
4741 tgttaagagg acttagtttg tgatgtaagg cactgtcagg aatggggggc gggccagggt
4801 gggaagagaa gaaatagcag agcctatttt ggtgaggttt tttgttttta agtcaaagaa
4861 gactcagtat gctttccctg aggaatgaaa aagggattga ggagttgcct gactcctggg
4921 tgggtggggt acaggcagtt aggtgctgaa tgaagctgcc atccttgctg cagcttctaa
4981 ctggtaaaaa gatccaggga tggagatggg aaggttagaa aggcagccct cacctctgag
5041 gacagaggcc ggggtccagg cccgtgggcg caaaggtgcc tcatagcata gccagcattc
5101 agcacacaca aacctactgc ccacatttgg gctcagggtt ggccatttgc tagttctgct
5161 gccctcttaa gatctgactg ccaaataaat catcctcatg tcctt
```

FIG. 2D

Polypeptide sequence of human phospholipase C gamma 1 (PLCG1; SEQ ID NO: 2). Corresponds to coding sequence defined by positions 122-3997 in DNA sequence above. Accession nos. NM_002660 and NP_002651.

MAGAASPCANGCGPGAPSDAEVLHLCRSLEVGTVMTLFYSKKSQRPERKTFQVKLETRQITWSRGADKIEGA
IDIREIKEIRPGKTSRDFDRYQEDPAFRPDQSHCFVILYGMEFRLKTLSLQATSEDEVNMWIKGLTWLMEDT
LQAPTPLQIERWLRKQFYSVDRNREDRISAKDLKNMLSQVNYRVPNMRFLRERLTDLEQRSGDITYGQFAQL
YRSLMYSAQKTMDLPFLEASTLRAGERPELCRVSLPEFQQFLLDYQGELWAVDRLQVQEFMLSFLRDPLREI
EEPYFFLDEFVTFLFSKENSVWNSQLDAVCPDTMNNPLSHYWISSSHNTYLTGDQFSSESSLEAYARCLRMG
CRCIELDCWDGPDGMPVIYHGHTLTTKIKFSDVLHTIKEHAFVASEYPVILSIEDHCSIAQQRNMAQYFKKV
LGDTLLTKPVEISADGLPSPNQLKRKILIKHKKLAEGSAYEEVPTSMMYSENDISNSIKNGILYLEDPVNHE
WYPHYFVLTSSKIYYSEETSSDQGNEDEEEPKEVSSSTELHSNEKWFHGKLGAGRDGRHIAERLLTEYCIET
GAPDGSFLVRESETFVGDYTLSFWRNGKVQHCRIHSRQDAGTPKFFLTDNLVFDSLYDLITHYQQVPLRCNE
FEMRLSEPVPQTNAHESKEWYHASLTRAQAEHMLMRVPRDGAFLVRKRNEPNSYAISFRAEGKIKHCRVQQE
GQTVMLGNSEFDSLVDLISYYEKHPLYRKMKLRYPINEEALEKIGTAEPDYGALYEGRNPGFYVEANPMPTF
KCAVKALFDYKAQREDELTFIKSAIIQNVEKQEGGWWRGDYGGKKQLWFPSNYVEEMVNPVALEPEREHLDE
NSPLGDLLRGVLDVPACQIAIRPEGKNNRLFVFSISMASVAHWSLDVAADSQEELQDWVKKIREVAQTADAR
LTEGKIMERRKKIALELSELVVYCRPVPFDEEKIGTERACYRDMSSFPETKAEKYVNKAKGKKFLQYNRLQL
SRIYPKGQRLDSSNYDPLPMWICGSQLVALNFQTPDKPMQMNQALFMTGRHCGYVLQPSTMRDEAFDPFDKS
SLRGLEPCAISIEVLGARHLPKNGRGIVCPFVEIEVAGAEYDSTKQKTEFVVDNGLNPVWPAKPFHFQISNP
EFAFLRFVVYEEDMFSDQNFLAQATFPVKGLKTGYRAVPLKNNYSEDLELASLLIKIDIFPAKQENGDLSPF
SGTSLRERGSDASGQLFHGRAREGSFESRYQQPFEDFRISQEHLADHFDSRERRAPRRTRVNGDNRL

FIG. 2E

DNA sequence of human phospholipase C gamma 2 (PLCG2; SEQ ID NO: 3).
Coding sequence defined by positions 153-3911. Accession no. NM_002661.

```
   1 gaattcggcg ctgagtgacc cgagtcggga cgcgggctgc gcgcgcggga ccccggagcc
  61 caaacccggg gcaggcgggc agctgtgccc gggcggcacg gccagcttcc tgatttctcc
 121 cgattccttc cttctccctg gagcggccga caatgtccac cacggtcaat gtagattccc
 181 ttgcggaata tgagaagagc cagatcaaga gagccctgga gctggggacg gtgatgactg
 241 tgttcagctt ccgcaagtcc acccccgagc ggagaaccgt ccaggtgatc atggagacgc
 301 ggcaggtggc ctggagcaag accgccgaca agatcgaggg cttcttggat atcatggaaa
 361 taaaagaaat ccgcccaggg aagaactcca aagatttcga gcgagcaaaa gcagttcgcc
 421 agaaagaaga ctgctgcttc accatcctat atggcactca gttcgtcctc agcacgctca
 481 gcttggcagc tgactctaaa gaggatgcag ttaactggct ctctggcttg aaaatcttac
 541 accaggaagc gatgaatgcg tccacgccca ccattatcga gagttggctg agaaagcaga
 601 tatattctgt ggatcaaacc agaagaaaca gcatcagtct ccgagagttg aagaccatct
 661 tgcccctgat caactttaaa gtgagcagtg ccaagttcct taaagataag tttgtggaaa
 721 taggagcaca caaagatgag ctcagctttg aacagttcca tctcttctat aaaaaactta
 781 tgtttgaaca gcaaaaatcg attctcgatg aattcaaaaa ggattcgtcc gtgttcatcc
 841 tggggaacac tgacaggccg gatgcctctg ctgtttacct gcatgacttc cagaggtttc
 901 tcatacatga acagcaggag cattgggctc aggatctgaa caaagtccgt gagcggatga
 961 caaagttcat tgatgacacc atgcgtgaaa ctgctgagcc tttcttgttt gtggatgagt
1021 tcctcacgta cctgttttca cgagaaaaca gcatctggga tgagaagtat gacgcggtgg
1081 acatgcagga catgaacaac cccctgtctc attactggat ctcctcgtca cataacacgt
1141 accttacagg tgaccagctg cggagcgagt cgtccccaga agcttacatc cgctgcctgc
1201 gcatgggctg tcgctgcatt gaactggact gctgggacgg gcccgatggg aagccggtca
1261 tctaccatgg ctggacgcgg actaccaaga tcaagtttga tgacgtcgtg caggccatca
1321 aagaccacgc ctttgttacc tcgagcttcc cagtgatcct gtccatcgag gagcactgca
1381 gcgtggagca acagcgtcac atggccaagg ccttcaagga agtatttggc gacctgctgt
```

FIG. 3A 1441 tgacgaagcc cacggaggcc agtgctgacc agctgccctc gcccagccag ctgcgggaga
1501 agatcatcat caagcataag aagctgggcc cccgaggcga tgtggatgtc aacatggagg
1561 acaagaagga cgaacacaag caacaggggg agctgtacat gtgggattcc attgaccaga
1621 aatggactcg gcactactgc gccattgctg atgccaagct gtccttcagt gatgacattg
1681 aacagactat ggaggaggaa gtgccccagg atataccccc tacagaacta cattttgggg
1741 agaaatggtt ccacaagaag gtggagaaga ggacgagtgc cgagaagttg ctgcaggaat
1801 actgcatgga gacggggggc aaggatggca ccttcctggt tcgggagagc gagaccttcc
1861 ccaatgacta caccctgtcc ttctggcggt caggccgggt ccagcactgc cggatccgct
1921 ccaccatgga gggcgggacc ctgaaatact acttgactga caacctgagg ttcaggagga
1981 tgtatgccct catccagcac taccgcgaga cgcacctgcc gtgcgccgag ttcgagctgc
2041 ggctcacgga ccctgtgccc aaccccaacc cccacgagtc caagccgtgg tactatgaca
2101 gcctgagccg cggagaggca gaggacatgc tgatgaggat tccccgggac ggggccttcc
2161 tgatccggaa gcgagagggg agcgactcct atgccatcac cttcagggct aggggcaagg
2221 taaagcattg tcgcatcaac cgggacggcc ggcactttgt gctggggacc tccgcctatt
2281 ttgagagtct ggtggagctc gtcagttact acgagaagca ttcactctac cgaaagatga
2341 gactgcgcta ccccgtgacc cccgagctcc tggagcgcta caatacggaa agagatataa
2401 actccctcta cgacgtcagc agaatgtatg tggatcccag tgaaatcaat ccgtccatgc
2461 ctcagagaac cgtgaaagct ctgtatgact acaaagccaa gcgaagcgat gagctgagct
2521 tctgccgtgg tgccctcatc cacaatgtct ccaaggagcc cgggggctgg tggaaaggag
2581 actatggaac caggatccag cagtacttcc catccaacta cgtcgaggac atctcaactg
2641 cagacttcga ggagctagaa aagcagatta ttgaagacaa tcccttaggg tctctttgca
2701 gaggaatatt ggacctcaat acctataacg tcgtgaaagc ccctcaggga aaaaaccaga
2761 agtcctttgt cttcatcctg gagcccaagg agcagggcga tcctccggtg gagtttgcca
2821 cagacagggt ggaggagctc tttgagtggt ttcagagcat ccgagagatc acgtggaaga
2881 ttgacagcaa ggagaacaac atgaagtact gggagaagaa ccagtccatc gccatcgagc
2941 tctctgacct ggttgtctac tgcaaaccaa ccagcaaaac caaggacaac ttagaaaatc
3001 ctgacttccg agaaatccgc tcctttgtgg agacgaaggc tgacagcatc atcagacaga

FIG. 3B

```
3061 agcccgtcga cctcctgaag tacaatcaaa agggcctgac ccgcgtctac ccaaagggac
3121 aaagagttga ctcttcaaac tacgacccct tccgcctctg gctgtgcggt tctcagatgg
3181 tggcactcaa tttccagacg gcagataagt acatgcagat gaatcacgca ttgttttctc
3241 tcaacgggcg cacgggctac gttctgcagc ctgagagcat gaggacagag aaatatgacc
3301 cgatgccacc cgagtcccag aggaagatcc tgatgacgct gacagtcaag gttctcggtg
3361 ctcgccatct ccccaaactt ggacgaagta ttgcctgtcc ctttgtagaa gtggagatct
3421 gtggagccga gtatggcaac aacaagttca agacgacggt tgtgaatgat aatggcctca
3481 gccctatctg ggctccaaca caggagaagg tgacatttga aatttatgac ccaaacctgg
3541 catttctgcg ctttgtggtt tatgaagaag atatgttcag cgatcccaac tttcttgctc
3601 atgccactta ccccattaaa gcagtcaaat caggattcag gtccgttcct ctgaagaatg
3661 ggtacagcga ggacatagag ctggcttccc tcctggtttt ctgtgagatg cggccagtcc
3721 tggagagcga agaggaactt tactcctcct gtcgccagct gaggaggcgg caagaagaac
3781 tgaacaacca gctctttctg tatgacacac accagaactt gcgcaatgcc aaccgggatg
3841 ccctggttaa agagttcagt gttaatgaga accactccag ctgtaccagg agaaatgcaa
3901 caagaggtta agagagaaga gagtcagcaa cagcaagttt tactcataga agctggggta
3961 tgtgtgtaag ggtattgtgt gtgtgcgcat gtgtgtttgc atgtaggaga acgtgcccta
4021 ttcacactct gggaagacgc taatctgtga catcttttct tcaagcctgc catcaaggac
4081 atttcttaag acccaactgg catgagttgg ggtaatttcc tattattttc atcttggaca
4141 acttctaact tatatcttta tagaggattc cccaaaatgt gctcctcatt tttggcctct
4201 catgttccaa acctcattga ataaaaagca atgaaaacct tg
```

FIG. 3C

Polypeptide sequence of human phospholipase C gamma 2 (PLCG2; SEQ ID NO: 4). Corresponds to coding sequence defined by positions 153-3911 in DNA sequence above. Accession nos. NM_002661 and NP_002652.

MSTTVNVDSLAEYEKSQIKRALELGTVMTVFSFRKSTPERRTVQVIMETRQVAWSKTADKIEGFLDIMEIKE
IRPGKNSKDFERAKAVRQKEDCCFTILYGTQFVLSTLSLAADSKEDAVNWLSGLKILHQEAMNASTPTIIES
WLRKQIYSVDQTRRNSISLRELKTILPLINFKVSSAKFLKDKFVEIGAHKDELSFEQFHLFYKKLMFEQQKS
ILDEFKKDSSVFILGNTDRPDASAVYLHDFQRFLIHEQQEHWAQDLNKVRERMTKFIDDTMRETAEPFLFVD
EFLTYLFSRENSIWDEKYDAVDMQDMNNPLSHYWISSSHNTYLTGDQLRSESSPEAYIRCLRMGCRCIELDC
WDGPDGKPVIYHGWTRTTKIKFDDVVQAIKDHAFVTSSFPVILSIEEHCSVEQQRHMAKAFKEVFGDLLLTK
PTEASADQLPSPSQLREKIIIKHKKLGPRGDVDVNMEDKKDEHKQQGELYMWDSIDQKWTRHYCAIADAKLS
FSDDIEQTMEEEVPQDIPPTELHFGEKWFHKKVEKRTSAEKLLQEYCMETGGKDGTFLVRESETFPNDYTLS
FWRSGRVQHCRIRSTMEGGTLKYYLTDNLRFRRMYALIQHYRETHLPCAEFELRLTDPVPNPNPHESKPWYY
DSLSRGEAEDMLMRIPRDGAFLIRKREGSDSYAITFRARGKVKHCRINRDGRHFVLGTSAYFESLVELVSYY
EKHSLYRKMRLRYPVTPELLERYNTERDINSLYDVSRMYVDPSEINPSMPQRTVKALYDYKAKRSDELSFCR
GALIHNVSKEPGGWWKGDYGTRIQQYFPSNYVEDISTADFEELEKQIIEDNPLGSLCRGILDLNTYNVVKAP
QGKNQKSFVFILEPKEQGDPPVEFATDRVEELFEWFQSIREITWKIDSKENNMKYWEKNQSIAIELSDLVVY
CKPTSKTKDNLENPDFREIRSFVETKADSIIRQKPVDLLKYNQKGLTRVYPKGQRVDSSNYDPFRLWLCGSQ
MVALNFQTADKYMQMNHALFSLNGRTGYVLQPESMRTEKYDPMPPESQRKILMTLTVKVLGARHLPKLGRSI
ACPFVEVEICGAEYGNNKFKTTVVNDNGLSPIWAPTQEKVTFEIYDPNLAFLRFVVYEEDMFSDPNFLAHAT
YPIKAVKSGFRSVPLKNGYSEDIELASLLVFCEMRPVLESEEELYSSCRQLRRRQEELNNQLFLYDTHQNLR
NANRDALVKEFSVNENHSSCTRRNATRG

FIG. 3D

METHOD FOR IDENTIFYING COMPOUNDS FOR TREATMENT OF PAIN

CROSS REFERENCE TO RELATED APPLICATIONS

This application is the 371 National Phase of International Application No. PCT/CA2005/000738, filed May 13, 2005, which was published in English under PCT Article 21(2) as International Publication No. WO 2005/110490. This application further claims priority from International application No. PCT/CA2004/000726 filed May 14, 2004. This application further claims the benefit, under 35 U.S.C. 119(e), of U.S. provisional patent application Ser. No. 60/627,174 filed Nov. 15, 2004. All of these applications are incorporated herein by reference in their entirety.

FIELD OF THE INVENTION

The invention relates to the modulation of activity, function and/or expression of phospholipase C gamma ($PLC_\gamma$) in a subject and uses thereof, such as for treating and preventing and pain.

BACKGROUND OF THE INVENTION

The need for new and improved methods and agents for pain treatment is a significant ongoing concern in medicine. Acute pain, e.g. related to injury or disease, can be severe and have critical effects on patient recovery. An even greater concern is chronic pain, which affects a large proportion of the population, causing not only significant discomfort, but can result in low self-esteem, depression, anger, and can interfere with or completely prevent a sufferer from typical daily activities.

While a number of studies have been done in this area, many mechanisms and pathways involved in pain sensation remain poorly understood. There remains a continued need to provide new strategies of therapeutic intervention for pain treatment.

SUMMARY OF THE INVENTION

The invention relates to methods of treating and/or preventing pain. The invention further relates to methods of modulating (e.g. inhibiting) activity, expression, and/or function of a phospholipase C gamma ($PLC_\gamma$) in a subject.

According to one aspect of the present invention, there is provided a method of treating or preventing pain in a subject, the method comprising modulating activity, function and/or expression of a $PLC_\gamma$ in the subject.

According to another aspect of the present invention, there is provided a method of treating or preventing pain in a subject, the method comprising administering to the subject an agent capable of modulating activity, function and/or expression of a $PLC_\gamma$ in the subject.

According to still another aspect of the present invention, there is provided a method of treating or preventing pain in a subject, comprising administering to the subject a composition comprising: an agent capable of modulating activity, function and/or expression of a $PLC_\gamma$ in the subject; and a pharmaceutically acceptable carrier.

According to yet another aspect of the present invention, there is provided a composition for treatment or prevention of pain in a subject, comprising: an agent capable of modulating activity, function and/or expression of a $PLC_\gamma$ in the subject; and a pharmaceutically acceptable carrier.

According to a further aspect of the present invention, there is provided a package comprising an agent capable of modulating activity, function and/or expression of a $PLC_\gamma$ in a subject together with instructions for its use in the treatment or prevention of pain.

According to yet a further aspect of the present invention, there is provided a package comprising a composition comprising: an agent capable of modulating activity, function and/or expression of a $PLC_\gamma$ in a subject; and a pharmaceutically acceptable carrier, together with instructions for its use in the treatment or prevention of pain.

According to still a further aspect of the present invention, there is provided a use of an agent capable of modulating activity, function and/or expression of a $PLC_\gamma$ in a subject for the treatment or prevention of pain.

According to another aspect of the present invention, there is provided a use of an agent capable of modulating activity, function and/or expression of a $PLC_\gamma$ in a subject for the preparation of a medicament for the treatment or prevention of pain.

According to yet another aspect of the present invention, there is provided a use, for the treatment or prevention of pain, of a composition comprising: an agent capable of modulating activity, function and/or expression of a $PLC_\gamma$ in a subject; and a pharmaceutically acceptable carrier.

According to another aspect of the present invention, there is provided a method of identifying or characterizing an agent for treatment or prevention of pain, comprising determining $PLC_\gamma$ activity, function and/or expression in the presence of a test agent. In an embodiment, the method comprises contacting the test agent with a $PLC_\gamma$ or a cell having an activity, function and/or expression of a $PLC_\gamma$; and determining whether there is modulation (e.g. an inhibition) of the activity, function and/or expression of a $PLC_\gamma$ in the presence of the agent; wherein the modulation is an indication that the agent may be used for treatment or prevention of pain.

The invention further provides a method of identifying or characterizing a compound for treatment or prevention of pain, said method comprising: (a) contacting a test compound with a cell comprising a first nucleic acid comprising a transcriptionally regulatory element normally associated with a $PLC_\gamma$ gene, operably linked to a second nucleic acid comprising a reporter gene capable of encoding a reporter protein; and (b) determining whether reporter gene expression or reporter protein activity is decreased in the presence of said test compound; wherein said decrease in reporter gene expression or reporter protein activity being is an indication that said test compound may be used for treatment or prevention of pain.

The invention further provides a method of identifying or characterizing an agent for treatment or prevention of pain, comprising:

contacting the agent and a PLCγ ligand with a cell comprising a $PLC_\gamma$; and determining whether there is a decrease of the binding of the ligand to the $PLC_\gamma$ in the presence of the agent;

wherein the decrease is an indication that the agent may be used for treatment or prevention of pain.

The invention further provides a method of identifying or characterizing an agent for treatment or prevention of pain, comprising:

contacting the agent and a PLCγ ligand with a $PLC_\gamma$; and determining whether there is decrease of the binding of the ligand to the $PLC_\gamma$ in the presence of the agent;

wherein the decrease is an indication that the agent may be used for treatment or prevention of pain.

According to still another aspect of the present invention, there is provided a method for decreasing nociception in a subject, comprising modulating activity, function and/or expression of a $PLC_\gamma$ in the subject.

According to yet another aspect of the present invention, there is provided a method for decreasing nociception in a subject, comprising administering to the subject an agent capable of modulating activity, function and/or expression of a $PLC_\gamma$ in the subject.

According to a further aspect of the present invention, there is provided a method for decreasing nociception in a subject, comprising administering to the subject a composition comprising: an agent capable of modulating activity, function and/or expression of a $PLC_\gamma$ in the subject; and a pharmaceutically acceptable carrier.

In an embodiment, the above-mentioned modulation of $PLC_\gamma$ activity, function and/or expression is an inhibition of $PLC_\gamma$ activity or expression. In an embodiment the above-mentioned agent capable of modulating $PLC_\gamma$ activity, function and/or expression is an agent capable of inhibiting $PLC_\gamma$ activity, function and/or expression.

In an embodiment, the agent as defined herein may be a $PLC_\gamma$ inhibitor, an anti-$PLC_\gamma$ antibody, an antisense molecule, a siRNA, a siRNA-like molecule, or an inhibitor of binding of a ligand or binding partner to a PLCγ. For example, the $PLC_\gamma$ inhibitor may be tricyclodecan-9-yl-xanthogenate, 1-O-octadecyl-2-O-methyl-rac-glycero-3-phosphorylcholine, neomycin sulfate, spermine tetrahydrochloride, 1-[6-((17beta-3-methoxyestra-1,3,5(10)-trien-17-yl)amino)hexyl]-1H-pyrrole-2,5-dione, or 1-[6-((17beta-3-methoxyestra-1,3,5(10)-trien-17-yl)amino)hexyl]-2,5-pyrrolidinedione.

In an embodiment, the antisense molecule is a nucleic acid that is substantially complementary to a portion of an mRNA encoding a $PLC_\gamma$. In an embodiment, the antisense molecule is a nucleic acid that is substantially complementary to a nucleic acid comprising a nucleotide sequence capable of encoding a polypeptide having an amino acid sequence selected from SEQ ID NO:2 and SEQ ID NO:4. In a further embodiment, the antisense molecule is a nucleic acid that is substantially complementary to a nucleic acid comprising a nucleotide sequence selected from SEQ ID NO:1 and SEQ ID NO:3. In an embodiment, the above-noted portion of an mRNA comprises at least 5 contiguous bases.

In an embodiment, the siRNA or siRNA-like molecule is substantially identical to a portion of an mRNA encoding $PLC_\gamma$. In an embodiment, the siRNA or siRNA-like molecule is substantially identical to a portion of an mRNA corresponding to a DNA sequence capable of encoding a polypeptide having an amino acid sequence selected from SEQ ID NO:2 and SEQ ID NO:4. In a further embodiment, the siRNA or siRNA-like molecule is substantially identical to a portion of an mRNA corresponding to a DNA sequence selected from SEQ ID NO:1 and SEQ ID NO:3. In an embodiment, the siRNA or siRNA-like molecule comprises less than about 30 nucleotides, in a further embodiment about 21 to 23 nucleotides.

In embodiments, the pain is pain associated with neuropathic pain and/or CNS dysfunction.

In a further embodiment, pain may be neuropathic pain, somatic or visceral pain. For example, the neuropathic pain may be associated with a nerve or tract injury. In yet another embodiment, pain may be chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury or recurrent acute pain.

BRIEF DESCRIPTION OF THE DRAWINGS

FIG. 2: DNA (SEQ ID NO:1, FIGS. 2A-2D) and polypeptide (SEQ ID NO:2, FIG. 2E) sequences of human phospholipase C gamma 1 (PLCG1; accession nos. NM_002660 and NP_002651). Coding sequence is defined by positions 122-3997 of DNA sequence.

FIG. 3: DNA (SEQ ID NO:3, FIGS. 3A-3C) and polypeptide (SEQ ID NO:4,FIG. 3D) sequences of human phospholipase C gamma 2 (PLCG2; accession nos. NM_002661 and NP_002652). Coding sequence defined by positions 153-3911 of DNA sequence.

DETAILED DESCRIPTION OF THE INVENTION

Figure 1:
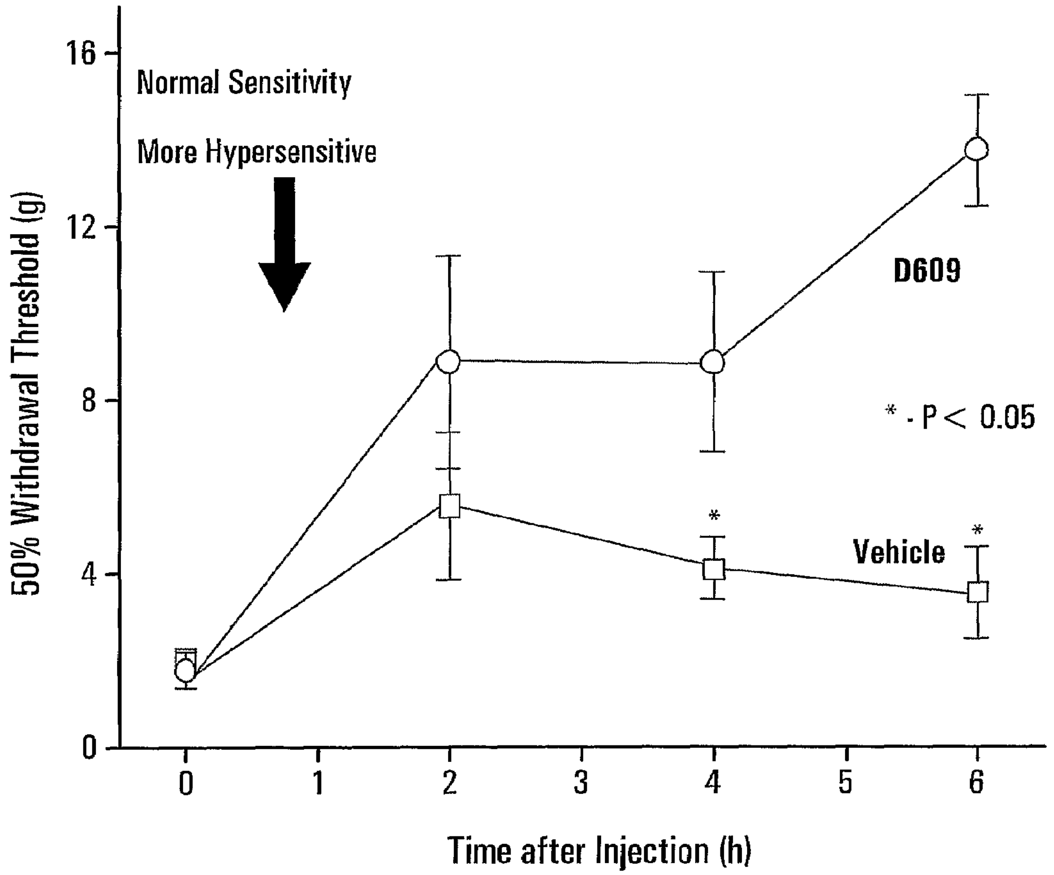
FIG. 1: Comparison between the 50% withdrawal threshold for pain hypersensitivity of rats treated with tricyclodecan-9-yl-xanthogenate (○) and a vehicle (□).

The invention provides a method for the prevention and/or treatment of pain in a subject. In embodiments, the subject may be a vertebrate or a mammal. In an embodiment, the subject is a mammal, for example a human. The method comprises inhibiting or decreasing the activity, function and/or expression of a phospholipase C gamma ($PLC_\gamma$) in a subject, e.g. in a cell or tissue of the subject, for example a central nervous system (CNS) neural cell or tissue. The method may comprise administering to the subject, systemic or local, an agent capable of modulating, e.g. inhibiting, activity, expression and/or function of a $PLC_\gamma$ as a means to attenuate pain. The agent may be administered before, at about the time of, or subsequent to the onset of pain.

In an embodiment, the CNS neural cell in which the $PLC_\gamma$ activity, function and/or expression is modulated may be located in the superficial dorsal horn or the spinal cord. In addition, the cell may also be transsynaptic to a peripheral nerve cell or sensory fiber from which a signal for pain originates.

The invention also relates to the treatment of acute and chronic pain, more specifically to the treatment of neuropathic pain. "Neuropathic pain", as used herein, refers to chronic pain associated with nerve injury (e.g. following crush, transection or compression of nerves or following nerve degeneration resulting from disease). Neuropathic pain may be associated with a nerve or tract injury. Moreover, the neuropathic pain may be associated with visceral and/or somatic pain.

In an embodiments, the pain may be associated with a condition chosen from chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, recurrent acute pain, and/or any combination of the above.

The invention further provides a method for decreasing nociception in a subject. The method comprises modulating activity, function and/or expression of a $PLC_γ$ in a subject to reduce nociception. "Nociception" as used herein refers to the sensory component of pain. Pain may be the result of various stimuli, including but not limited to pressure, injury, thermal stimuli or chemical (e.g. ionic) stimuli.

The agent includes, but is not limited to, that which directly or indirectly modifies the activity of the protein and that which modulates the production and/or stability of the protein (e.g. at the level of transcription, translation, maturation, post-translational modification, phosphorylation and degradation). For example, the agent may be a $PLC_γ$ inhibitor. In an embodiment, such an inhibitor may be a peptide or peptide-based compound (e.g. a peptidomimetic). In further embodiments, the agent may be an anti-$PLC_γ$ antibody which is capable of modulating the binding and/or catalytic activity of a $PLC_γ$. Examples of anti-$PLC_γ$ antibodies are described in for example Lee et al. (2002, *Mol. Vis.,* 8: 17-25) and Buckley et al. (2004, *J. Biol. Chem.,* 279: 41807-14). In a further embodiment, the agent may be an antisense molecule complementary to all or a portion of the mRNA encoding a $PLC_γ$. In a further embodiment, the agent may be an siRNA or siRNA-like molecule.

In a further embodiment, the above-mentioned inhibition is effected by the inhibition of a binding domain(s) of a $PLC_γ$. In such a case, the agent is an inhibitor of binding of a ligand or binding partner to a PLCγ. For example, binding of mitogen-activated protein kinases [e.g. extracellular signal-related kinase (ERK1 and ERK2)] to a PLCγ (e.g. to the D-domain) may be inhibited. As shown in Buckley et al., 2004, *J. Biol. Chem.,* 279:41807-41814, both ERK and phospho-ERK (which, like $PLC_γ$ are activated by BDNF binding of TrkB) bind the D domain of $PLC_γ$ and induce phosphorylation of this isozyme.

In one embodiment, the agent capable of modulating activity and/or expression of a $PLC_γ$ is a $PLC_γ$ inhibitor. Examples of $PLC_γ$ inhibitors include, but are not limited to, tricyclodecan-9-yl-xanthogenate, 1-O-octadecyl-2-O-methyl-rac-glycero-3-phosphorylcholine, neomycin sulfate, spermine tetrahydrochloride, 1-[6-((17beta-3-methoxyestra-1,3,5(10)-trien-17-yl)amino)hexyl]-1H-pyrrole-2,5-dione, or 1-[6-((17beta-3-methoxyestra-1,3,5(10)-trien-17-yl)amino) hexyl]-2,5-pyrrolidinedione. References describing the $PLC_γ$ inhibiting action of tricyclodecan-9-yl-xanthogenate (also referred to as D609) include: Monick, M. M. et al., 1999, *J. Immunol.* 162, 3005; Maragoudakis, M. E. et al., 1993, *Kidney Int.* 43, 147; Schutze, S. et al., 1992, *Cell* 71, 765; Muller-Decker, K., 1989, *Biochem. Biophys. Res. Commun.* 162, 198; Sauer, G. et al., 1984, *Proc. Natl. Acad. Sci. USA* 81, 3263. The aboved-mentioned $PLC_γ$ inhibitors are available from EMD Biosciences (a division of Calbiochem).

In another embodiment, the agent capable of modulating activity and/or expression of $PLC_γ$ is an anti-$PLC_γ$ antibody. Examples of anti-$PLC_γ$ antibodies are described in for example Lee et al. (2002, *Mol. Vis.,* 8: 17-25) and Buckley et al. (2004, *J. Biol. Chem.,* 279: 41807-14). To prepare such an anti-$PLC_γ$ antibody, a $PLC_γ$ or fragment, homolog, and/or variant thereof may be used to immunize a small mammal, e.g., a mouse or a rabbit, in order to raise antibodies which recognize a $PLC_γ$. An anti-$PLC_γ$ antibody may be either polyclonal or monoclonal. Methods to produce polyclonal or monoclonal antibodies are well known in the art. For a review, see Harlow and Lane (1988) *Antibodies: A Laboratory Manual*, Cold Spring Harbor Laboratory Press, Cold Spring Harbor, N.Y. and Yelton et al. (1981) *Ann. Rev. Biochem.* 50:657-690, both of which are herein incorporated by reference. For monoclonal antibodies, see Kohler and Milstein (1975) *Nature* 256:495-497, herein incorporated by reference.

"PLC gamma" or "$PLC_γ$" refers to a polypeptide possessing an activity capable of cleaving a phosphotidylinositol 4,5 bisphosphate to yield diacylglycerol and inositol 1,4,5-triphosphate. In embodiments, the $PLC_γ$ is selected from the PLCγ1 and PLCγ2 isoforms. Genes which encode human $PLC_γ$ polypeptides are described for example at NCBI accession Nos. M34667, NM_002660, NM_002661 and NM_182811. Examples of genes which encode human $PLC_γ$ polypeptides as well as the polypeptides they encode are set forth in FIGS. 2 and 3 and SEQ ID NOs:1-4. For a review of PLCγ activity see Carpenter and Ji (1999, *Experimental Cell Research,* 253: 15-24). PLCγ activity may be assayed by for example electrophoretic mobility shift assays (Noh et al., 1998, *Anticancer Research,* 18: 2643-8) and myo-inositol 1,4,5-triphosphate radioceptor assays (Shu et al., 2002, *J. Biol. Chem.,* 277: 18447-18453).

As noted above, a fragment, homolog and/or variant of a $PLC_γ$ which retains activity may also be used in the methods of the invention. Homologs include protein sequences which are substantially identical to the amino acid sequence of a $PLC_γ$, sharing significant structural and functional homology with a $PLC_γ$. Variants include, but are not limited to, proteins or peptides which differ from a $PLC_γ$ by any modifications, and/or amino acid substitutions, deletions or additions. Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of a $PLC_γ$ or a fragment or a portion of a homolog or variant of a $PLC_γ$.

Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monoclonal antibodies may also be in the form of immunoglobulin fragments, e.g., $F(ab)'_2$, Fab or Fab' fragments. The antibodies may be of any isotype, e.g., IgG or IgA, and polyclonal antibodies are of a single isotype or a mixture of isotypes. Anti-$PLC_γ$ antibodies may be produced and identified using standard immunological assays, e.g., Western blot analysis, dot blot assay, or ELISA.

Another class of compounds that can be used to limit $PLC_γ$ expression are compounds that lower the level of $PLC_γ$ transcripts. By doing so, these compounds limit the number of $PLC_γ$ polypeptides that can be produced and can therefore be use to treat or prevent pain. These compounds include, but are not limited to, dsRNA, siRNA, siRNA-like molecule, antisense oligonucleotide or ribozyme.

In an embodiment, expression of a nucleic acid encoding a polypeptide of interest, or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example Hammond et al. (2001), Sharp (2001), Caplen et al. (2001), Sedlak (2000) and published US patent applications 20020173478 (Gewirtz; published Nov. 21, 2002) and 20020132788 (Lewis et al.; published Nov. 7, 2002). Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. A siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA (Brown et al., 2002). Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in for example Brummelkamp et al. (2002), Lee et al. (2002), Miyagashi and Taira (2002), Paddison et al. (2002) Paul et al. (2002) Sui et al. (2002) and Yu et al. (2002). Various methods for introducing such vectors into cells, either in vitro or in vivo (e.g. gene therapy) are known in the art.

Accordingly, in an embodiment expression of a nucleic acid encoding a $PLC_{\gamma}$, or a fragment thereof, may be inhibited by introducing into or generating within a cell an siRNA or siRNA-like molecule corresponding to a nucleic acid encoding a polypeptide of interest, or a fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a $PLC_{\gamma}$, or a fragment or variant (or a fragment of a variant) thereof. Such a variant is capable of encoding a protein having activity similar to a $PLC_{\gamma}$. In embodiments, the sense strand of the siRNA or siRNA-like molecule is substantially identical to SEQ ID NOs: 1 or 3, or a fragment thereof (RNA having U in place of T residues of the DNA sequence).

In yet another embodiment, transformation of cells with antisense constructs may be used to inhibit expression of a $PLC_{\gamma}$. Antisense constructs are nucleic acid molecules that may be transcribed to provide an antisense molecule that is substantially complementary to all or a portion of the mRNA encoding a $PLC_{\gamma}$, so that expression of the antisense construct interferes with the expression of the $PLC_{\gamma}$. In an embodiment, the just noted antisense molecule is antisense to a DNA sequence coding a $PLC_{\gamma}$, in an embodiment, a human $PLC_{\gamma}$. In some embodiments, antisense constructs of the invention may therefore encode five or more contiguous nucleic acid-residues substantially complimentary to a contiguous portion of a nucleic acid sequence encoding a $PLC_{\gamma}$.

In further embodiments, polypeptides and nucleic acids which are substantially identical to those noted herein may be utilized in the context of the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs 1-4.

Substantially complementary nucleic acids are nucleic acids in which the "complement" of one molecule is substantially identical to the other molecule. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTEIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In alternative embodiments, the invention provides antisense molecules and ribozymes for exogenous administration to bind to, degrade and/or inhibit the translation of $PLC_\gamma$ mRNA. Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the $PLC_\gamma$ mRNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as inhibitors of the invention is disclosed in U.S. Pat. No. 5,932,435 (which is incorporated herein by reference).

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures that are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

The invention also provides pharmaceutical compositions (medicaments) comprising an agent capable of modulating activity and/or expression of a $PLC_\gamma$, and a pharmaceutically acceptable carrier. In an embodiment, such compositions include the agent, in a therapeutically or prophylactically effective amount sufficient to treat or attenuate pain, and a pharmaceutically acceptable carrier.

A "therapeutically effective amount" refers to an amount effective, at dosages and for periods of time necessary, to achieve the desired therapeutic result, such as reduction of pain. A therapeutically effective amount of an agent capable of modulating activity and/or expression of a $PLC_\gamma$, may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result, such as preventing or inhibiting onset of pain or increases in the severity of pain. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, intracranial, intrathecal, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active agent, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the agent capable of modulating activity and/or expression of a $PLC_\gamma$, can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active agent (e.g. an agent capable of modulating activity and/or expression of a $PLC_\gamma$) in the required amount in an appropriate solvent with one or a combination of ingredients enumerated above, as required, followed by filtered sterilization. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an agent capable of modulating activity and/or expression of a $PLC_\gamma$ in a subject, may be formulated with one or more additional compounds that enhance its solubility.

In another embodiment, an agent of the invention is administered such that it comes into contact with a CNS tissue or a CNS neuron. As used herein, the "central nervous system" or CNS is the portion of the nervous system comprising the brain and the spinal cord (e.g. in the lumbar region). By contrast, the "peripheral nervous system" or PNS is the portion of the nervous system other than the brain and the spinal cord. In a further embodiment, the CNS tissue is the superficial dorsal horn, in a further embodiment, a lamina I neuron. As such, in embodiments an agent of the invention can be administered to treat CNS cells in vivo via direct intracranial or intrathecal injection or injection into the cerebrospinal fluid. Alternatively, the agent can be administered systemically (e.g. intravenously, or orally) in a form capable of crossing the blood brain barrier and entering the CNS. "Neural" and "neuronal" are used herein interchangeably and both relate to neurons and the nervous system.

In a further embodiment of the present invention, therapeutic compositions of the present invention, comprising an agent capable of decreasing/inhibiting activity and/or expression of a $PLC_\gamma$ in a CNS cell may be provided in kits/containers or packages (e.g. commercial packages) which further comprise instructions for their use for the treatment of pain. Similarly, the invention provides a package comprising an agent capable of decreasing/inhibiting activity and/or expression of a $PLC_\gamma$ together with instructions for the prevention and/or treatment of pain.

The invention further provides a use of an agent capable of decreasing/inhibiting activity and/or expression of a $PLC_\gamma$ or a composition comprising an agent capable of decreasing/inhibiting activity and/or expression of a $PLC_\gamma$ for the prevention and/or treatment pain, or for the preparation of a medicament for the prevention and/or treatment of pain.

In another aspect, the invention relates to the use of $PLC_\gamma$ as a target in screening methods that may be used for the identification and characterization of agents capable of decreasing/inhibiting activity and/or expression of a $PLC_\gamma$. Therefore, the invention further provides a method of determining whether a candidate agent is capable of modulating activity and/or expression of a $PLC_\gamma$ in a subject, and in turn is useful for the prevention and treatment of pain. In an embodiment, the method comprises contacting a cell (e.g. a CNS-derived cell) with the candidate agent and determining whether $PLC_\gamma$ activity has been decreased or inhibited in the presence of the test agent. In a further embodiment, the assay may be carried out in a cell-free system, by providing a suitable preparation or sample of active $PLC_\gamma$, contacting the $PLC_\gamma$ with the candidate agent, and similarly determining whether its activity is inhibited or decreased in the presence of the test compound. In a further embodiment, the assay may comprise assessing whether a candidate compound inhibits the binding of a binding partner or ligand to a $PLC_\gamma$. In such a case, the method comprises contacting a $PLC_\gamma$ or a cell comprising a $PLC_\gamma$ with a candidate agent and the binding partner or ligand, and determining whether the binding of the binding partner or ligand to the $PLC_\gamma$ is decreased in the presence of the candidate or test compound. In embodiments, the binding partner or ligand is a mitogen-activated protein kinase or homolog or fragment thereof (such as ERK1 or ERK2, or a homolog or fragment thereof). In an embodiment, binding to the D-domain of $PLC_\gamma$ is determined.

Inhibition or a decrease of $PLC_\gamma$ activity or of the above-mentioned binding is indicative that the test agent may be used for the treatment or the prevention of pain.

As used herein, a "CNS-derived cell" is a cell isolated or derived from a CNS tissue, and in embodiments includes both primary neuronal cultures, immortalized neuronal cell lines, as well as accepted in vitro neuronal model systems (e.g. cells differentiated into neurons in vitro). In an embodiment, the above-mentioned cell possesses a $PLC_\gamma$ activity.

The above-mentioned method may be employed either with a single test agent or a plurality or library (e.g. a combinatorial library) of test agents. In the latter case, synergistic effects provided by combinations of agents may also be identified and characterized. The above-mentioned agents may be used for prevention and/or treatment of pain, or may be used as lead agents for the development and testing of additional agents having improved specificity, efficacy and/or pharmacological (e.g. pharmacokinetic) properties. In an embodiment the agent may be a prodrug which is altered into its active form at the appropriate site of action, e.g. in CNS tissue (e.g. in the spinal cord). In certain embodiments, one or a plurality of the steps of the screening/testing methods of the invention may be automated.

The invention further relates to methods for the identification and characterization of agents capable of decreasing/inhibiting $PLC_\gamma$ gene expression. Such a method may comprise determining $PLC_\gamma$ gene expression in the presence versus the absence of a test agent. Such gene expression may be determined by detection of the corresponding RNA or protein, or via the use of a suitable reporter construct comprising a transcriptional regulatory element(s) normally associated with such $PLC_\gamma$ gene, operably-linked to a reporter gene. A first nucleic acid sequence may "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, NY]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein.

The invention further provides a method for diagnosing or prognosticating pain associated with CNS dysfunction. In an embodiment, the pain associated with such CNS dysfunction is neuropathic pain. In an embodiment, the method comprises determining whether there is modulation of activity and/or expression of a $PLC_\gamma$ in a CNS neural cell relative to a corresponding control activity and/or expression of $PLC_\gamma$. In this particular method, a difference in the test level relative to a control level is an indication that the subject is experiencing pain associated with CNS dysfunction. In an embodiment, the method may comprise determining whether $PLC_\gamma$ activity and/or expression is modulated relative to a control activity and/or expression. In yet another embodiment, the $PLC_\gamma$ activity and/or expression can be selected from an established standard, such as a corresponding $PLC_\gamma$ activity and/or expression level determined in the subject at an earlier time; a corresponding $PLC_\gamma$ activity and/or expression level determined in said subject when the subject is experiencing less pain (relative to the current sensation of pain noted above) or substantially no pain; or a corresponding $PLC_\gamma$ activity and/or expression level determined in a control subject experiencing less pain (relative to the current sensation of pain in the test subject noted above) or substantially no pain. In an embodiment, a subject or control subject experiencing less pain or substantially no pain presents no evident lesions to his central or peripheral nervous system (e.g. neuropathic pain) or persistent pain.

For example, $PLC_\gamma$ activity and/or expression may be determined by administering, to a subject, an indicator compound (such as a compound indicative of activity and/or expression of $PLC_\gamma$) that is capable of contacting a CNS neural cell of that subject. Following the administration of the indicator compound, assessment of the in vivo signal associated with such indicator compound may be performed. In an embodiment, an indicator compound, such as an immunodetection-based reagent (e.g. antibody, single chain antibody or Fab fragment directed against the $PLC_\gamma$ polypeptide) or a suitable substrate which yields detectable products as a result of $PLC_\gamma$ activity, may be employed. Following injection of the indicator compound, an imaging technique may be performed to assess the in vivo signal associated with the indicator compound. The imaging technique may enable the assessment of the in vivo signal of the indicator compound.

In an embodiment, the methods of diagnosis/prognostication noted above may be performed in conjunction with the therapeutic/prophylactic methods noted above, for preventing or treating pain in a subject. Such a method thus comprises the diagnosis or prognostication of pain and modulation of activity and/or expression of a $PCL_γ$ in the subject, thereby to prevent or treat pain.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Eleven adult, Sprague-Dawley rats received an experimental chronic constriction injury to the sciatic nerve (Mosconi & Kruger, 1996, *Pain* 64:37-57). Pain hypersensitivity, indicative of neuropathic pain, increased progressively over a two week interval and was monitored using the Von Frey technique (Chaplan et al., 1994, *J. Neurosci. Methods* 53:55-63). Following the development of allodynia (characterized by a 50% withdrawal threshold ($WD_{50}$) of ≦2.0 g), rats were administered 500 ng tricyclodecan-9-yl-xanthogenate by intrathecal catheter, the tricyclodecan-9-yl-xanthogenate was prepared in a solution of saline (0.9% NaCl) with 10% v/v dimethyl sulfoxide. Tricyclodecan-9-yl-xanthogenate is available from EMD Biosciences (a division of Calbiochem). A solution of saline (0.9% NaCl) with 10% v/v dimethyl sulfoxide was injected into control rats as a vehicle. The volume of the vehicle administered was the same as for the $PLC_γ$ inhibitor solution.

Seven allodynic rats received single intrathecal injections of a vehicle, whereas 4 rats received single injections of tricyclodecan-9-yl-xanthogenate; the mean $WD_{50}$ for both groups was 1.9±0.2 g prior to injections. In as little as 4 hours post-injection, the $WD_{50}$ of rats administered tricyclodecan-9-yl-xanthogenate was significantly different from those that received the vehicle (tricyclodecan-9-yl-xanthogenate, 8.8±2.1 g vs. vehicle, 4.1±0.7 g; $p<0.05$), and significantly different from the initial, pre-injection $WD_{50}$ ($p<0.05$, mixed design ANOVA). This significant reduction of pain hypersensitivity persisted for greater than 6 hours.

Throughout this application, various references are referred to describe more fully the state of the art to which this invention pertains. The disclosures of these references are hereby incorporated by reference into the present disclosure.

The invention claimed is:

1. A method of identifying an agent for treatment of pain, comprising:

contacting the agent with a cell expressing a PLCγ; and determining whether there is inhibition of activity of said PLCγ in the presence of the agent, wherein inhibition of said activity is an indication that the agent may be used for the treatment of pain.

2. A method of identifying an agent for treatment of pain, comprising:

contacting the agent with a PLCγ; and determining whether there is inhibition of the activity of the PLCγ in the presence of the agent, wherein inhibition of said activity is an indication that the agent may be used for treatment of pain.

3. The method of claim 1, wherein the method comprises determining whether the agent inhibits the activity of said PLCγ in a CNS cell or tissue.

4. The method of claim 3, wherein the CNS cell or tissue is a spinal cord cell or tissue.

5. The method of claim 3, wherein a pain signal originates in a PNS cell or sensory fiber transsynaptic to the CNS cell.

6. The method of claim 1, wherein the pain is neuropathic pain.

7. The method of claim 6, wherein the neuropathic pain is associated with a nerve or tract injury.

8. The method of claim 6, wherein the neuropathic pain is selected from the group consisting of somatic and visceral pain.

9. The method of claim 1, wherein the pain is selected from the group consisting of chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and recurrent acute pain.

10. The method of claim 2, wherein the pain is neuropathic pain.

11. The method of claim 10, wherein the neuropathic pain is associated with a nerve or tract injury.

12. The method of claim 10, wherein the neuropathic pain is selected from the group consisting of somatic and visceral pain.

13. The method of claim 2, wherein the pain is selected from the group consisting of chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and recurrent acute pain.

* * * * *

SEQUENCE LISTING

```
<160> NUMBER OF SEQ ID NOS: 4

<210> SEQ ID NO 1
<211> LENGTH: 5205
<212> TYPE: DNA
<213> ORGANISM: Homo sapiens
<220> FEATURE:
<221> NAME/KEY: CDS
<222> LOCATION: (122)..(3997)

<400> SEQUENCE: 1

gagccgccgc cgggtcccgc tcgtctgccg cctcagcctc agccccaacc tcagccgccg      60

ccgttgcgct tgctcccggg cggtcctggc ctgtgccgcc gccgccccca gcgtcggagc     120

c atg gcg ggc gcc gcg tcc cct tgc gcc aac ggc tgc ggg ccc ggc gcg     169
  Met Ala Gly Ala Ala Ser Pro Cys Ala Asn Gly Cys Gly Pro Gly Ala
  1               5                   10                  15

ccc tcg gac gcc gag gtg ctg cac ctc tgc cgc agc ctc gag gtg ggc       217
Pro Ser Asp Ala Glu Val Leu His Leu Cys Arg Ser Leu Glu Val Gly
            20                  25                  30

acc gtc atg act ttg ttc tac tcc aag aag tcg cag cga ccc gag cgg       265
Thr Val Met Thr Leu Phe Tyr Ser Lys Lys Ser Gln Arg Pro Glu Arg
        35                  40                  45

aag acc ttc cag gtc aag ctg gag acg cgc cag atc acg tgg agc cgg       313
Lys Thr Phe Gln Val Lys Leu Glu Thr Arg Gln Ile Thr Trp Ser Arg
    50                  55                  60

ggc gcc gac aag atc gag ggg gcc att gac att cgt gaa att aag gag       361
Gly Ala Asp Lys Ile Glu Gly Ala Ile Asp Ile Arg Glu Ile Lys Glu
65                  70                  75                  80

atc cgc cca ggg aag acc tca cgg gac ttt gat cgc tat caa gag gac       409
Ile Arg Pro Gly Lys Thr Ser Arg Asp Phe Asp Arg Tyr Gln Glu Asp
                85                  90                  95
```

-continued

```
cca gct ttc cgg ccg gac cag tca cat tgc ttt gtc att ctc tat gga      457
Pro Ala Phe Arg Pro Asp Gln Ser His Cys Phe Val Ile Leu Tyr Gly
            100                 105                 110

atg gaa ttt cgc ctg aaa acg ctg agc ctg caa gcc aca tct gag gat      505
Met Glu Phe Arg Leu Lys Thr Leu Ser Leu Gln Ala Thr Ser Glu Asp
        115                 120                 125

gaa gtg aac atg tgg atc aag ggc tta act tgg ctg atg gag gat aca      553
Glu Val Asn Met Trp Ile Lys Gly Leu Thr Trp Leu Met Glu Asp Thr
    130                 135                 140

ttg cag gca ccc aca ccc ctg cag att gag agg tgg ctc cgg aag cag      601
Leu Gln Ala Pro Thr Pro Leu Gln Ile Glu Arg Trp Leu Arg Lys Gln
145                 150                 155                 160

ttt tac tca gtg gat cgg aat cgt gag gat cgt ata tca gcc aag gac      649
Phe Tyr Ser Val Asp Arg Asn Arg Glu Asp Arg Ile Ser Ala Lys Asp
                165                 170                 175

ctg aag aac atg ctg tcc cag gtc aac tac cgg gtc ccc aac atg cgc      697
Leu Lys Asn Met Leu Ser Gln Val Asn Tyr Arg Val Pro Asn Met Arg
            180                 185                 190

ttc ctc cga gag cgg ctg acg gac ctg gag cag cgc agc ggg gac atc      745
Phe Leu Arg Glu Arg Leu Thr Asp Leu Glu Gln Arg Ser Gly Asp Ile
        195                 200                 205

acc tac ggg cag ttt gct cag ctg tac cgc agc ctc atg tac agc gcc      793
Thr Tyr Gly Gln Phe Ala Gln Leu Tyr Arg Ser Leu Met Tyr Ser Ala
    210                 215                 220

cag aag acg atg gac ctc ccc ttc ttg gaa gcc agt act ctg agg gct      841
Gln Lys Thr Met Asp Leu Pro Phe Leu Glu Ala Ser Thr Leu Arg Ala
225                 230                 235                 240

ggg gag cgg ccg gag ctt tgc cga gtg tcc ctt cct gag ttc cag cag      889
Gly Glu Arg Pro Glu Leu Cys Arg Val Ser Leu Pro Glu Phe Gln Gln
                245                 250                 255

ttc ctt ctt gac tac cag ggg gag ctg tgg gct gtt gat cgc ctc cag      937
Phe Leu Leu Asp Tyr Gln Gly Glu Leu Trp Ala Val Asp Arg Leu Gln
            260                 265                 270

gtg cag gag ttc atg ctc agc ttc ctc cga gac ccc tta cga gag atc      985
Val Gln Glu Phe Met Leu Ser Phe Leu Arg Asp Pro Leu Arg Glu Ile
        275                 280                 285

gag gag cca tac ttc ttc ctg gat gag ttt gtc acc ttc ctg ttc tcc     1033
Glu Glu Pro Tyr Phe Phe Leu Asp Glu Phe Val Thr Phe Leu Phe Ser
    290                 295                 300

aaa gag aac agt gtg tgg aac tcg cag ctg gat gca gta tgc ccg gac     1081
Lys Glu Asn Ser Val Trp Asn Ser Gln Leu Asp Ala Val Cys Pro Asp
305                 310                 315                 320

acc atg aac aac cct ctt tcc cac tac tgg atc tcc tcc tcg cac aac     1129
Thr Met Asn Asn Pro Leu Ser His Tyr Trp Ile Ser Ser Ser His Asn
                325                 330                 335

acg tac ctg acc ggg gac cag ttc tcc agt gag tcc tcc ttg gaa gcc     1177
Thr Tyr Leu Thr Gly Asp Gln Phe Ser Ser Glu Ser Ser Leu Glu Ala
            340                 345                 350

tat gct cgc tgc ctg cgg atg ggc tgt cgc tgc att gag ttg gac tgc     1225
Tyr Ala Arg Cys Leu Arg Met Gly Cys Arg Cys Ile Glu Leu Asp Cys
        355                 360                 365

tgg gac ggc ccg gat ggg atg cca gtt att tac cat ggg cac acc ctt     1273
Trp Asp Gly Pro Asp Gly Met Pro Val Ile Tyr His Gly His Thr Leu
    370                 375                 380

acc acc aag atc aag ttc tca gat gtc ctg cac acc atc aag gag cat     1321
Thr Thr Lys Ile Lys Phe Ser Asp Val Leu His Thr Ile Lys Glu His
385                 390                 395                 400

gcc ttt gtg gcc tca gag tac cca gtc atc ctg tcc att gag gac cac     1369
Ala Phe Val Ala Ser Glu Tyr Pro Val Ile Leu Ser Ile Glu Asp His
```

-continued

```
            405                 410                 415

tgc agc att gcc cag cag aga aac atg gcc caa tac ttc aag aag gtg     1417
Cys Ser Ile Ala Gln Gln Arg Asn Met Ala Gln Tyr Phe Lys Lys Val
            420                 425                 430

ctg ggg gac aca ctc ctc acc aag ccc gtg gag atc tct gcc gac ggg     1465
Leu Gly Asp Thr Leu Leu Thr Lys Pro Val Glu Ile Ser Ala Asp Gly
        435                 440                 445

ctc ccc tca ccc aac cag ctt aag agg aag atc ctc atc aag cac aag     1513
Leu Pro Ser Pro Asn Gln Leu Lys Arg Lys Ile Leu Ile Lys His Lys
    450                 455                 460

aag ctg gct gag ggc agt gcc tac gag gag gtg cct aca tcc atg atg     1561
Lys Leu Ala Glu Gly Ser Ala Tyr Glu Glu Val Pro Thr Ser Met Met
465                 470                 475                 480

tac tct gag aac gac atc agc aac tct atc aag aat ggc atc ctc tac     1609
Tyr Ser Glu Asn Asp Ile Ser Asn Ser Ile Lys Asn Gly Ile Leu Tyr
                485                 490                 495

ctg gag gac cct gtg aac cac gaa tgg tat ccc cac tac ttt gtt ctg     1657
Leu Glu Asp Pro Val Asn His Glu Trp Tyr Pro His Tyr Phe Val Leu
            500                 505                 510

acc agc agc aag atc tac tac tct gag gag acc agc agt gac cag ggc     1705
Thr Ser Ser Lys Ile Tyr Tyr Ser Glu Glu Thr Ser Ser Asp Gln Gly
        515                 520                 525

aac gag gat gag gag gag ccc aag gag gtc agc agc agc aca gag ctg     1753
Asn Glu Asp Glu Glu Glu Pro Lys Glu Val Ser Ser Ser Thr Glu Leu
    530                 535                 540

cac tcc aat gag aag tgg ttc cat ggg aag cta ggg gca ggg cgt gac     1801
His Ser Asn Glu Lys Trp Phe His Gly Lys Leu Gly Ala Gly Arg Asp
545                 550                 555                 560

ggg cgt cac atc gct gag cgc ctg ctt act gag tac tgc atc gag acc     1849
Gly Arg His Ile Ala Glu Arg Leu Leu Thr Glu Tyr Cys Ile Glu Thr
                565                 570                 575

gga gcc cct gac ggc tcc ttc ctc gtg cga gag agt gag acc ttc gtg     1897
Gly Ala Pro Asp Gly Ser Phe Leu Val Arg Glu Ser Glu Thr Phe Val
            580                 585                 590

ggc gac tac acg ctc tct ttc tgg cgg aac ggg aaa gtc cag cac tgc     1945
Gly Asp Tyr Thr Leu Ser Phe Trp Arg Asn Gly Lys Val Gln His Cys
        595                 600                 605

cgt atc cac tcc cgg caa gat gct ggg acc ccc aag ttc ttc ttg aca     1993
Arg Ile His Ser Arg Gln Asp Ala Gly Thr Pro Lys Phe Phe Leu Thr
    610                 615                 620

gac aac ctc gtc ttt gac tcc ctc tat gac ctc atc acg cac tac cag     2041
Asp Asn Leu Val Phe Asp Ser Leu Tyr Asp Leu Ile Thr His Tyr Gln
625                 630                 635                 640

cag gtg ccc ctg cgc tgt aat gag ttt gag atg cga ctt tca gag cct     2089
Gln Val Pro Leu Arg Cys Asn Glu Phe Glu Met Arg Leu Ser Glu Pro
                645                 650                 655

gtc cca cag acc aac gcc cac gag agc aaa gag tgg tac cac gcg agc     2137
Val Pro Gln Thr Asn Ala His Glu Ser Lys Glu Trp Tyr His Ala Ser
            660                 665                 670

ctg acc aga gca cag gct gag cac atg cta atg cgc gtc cct cgt gat     2185
Leu Thr Arg Ala Gln Ala Glu His Met Leu Met Arg Val Pro Arg Asp
        675                 680                 685

ggg gcc ttc ctg gtg cgg aag cgg aat gaa ccc aac tca tat gcc atc     2233
Gly Ala Phe Leu Val Arg Lys Arg Asn Glu Pro Asn Ser Tyr Ala Ile
    690                 695                 700

tct ttc cgg gct gag ggc aag atc aag cat tgc cgt gtc cag caa gag     2281
Ser Phe Arg Ala Glu Gly Lys Ile Lys His Cys Arg Val Gln Gln Glu
705                 710                 715                 720

ggc cag aca gtg atg cta ggg aac tcg gag ttc gac agc ctt gtt gac     2329
```

-continued

Gly Gln Thr Val Met Leu Gly Asn Ser Glu Phe Asp Ser Leu Val Asp
725 730 735 ctc atc agc tac tat gag aaa cac ccg cta tac cgc aag atg aag ctg 2377
Leu Ile Ser Tyr Tyr Glu Lys His Pro Leu Tyr Arg Lys Met Lys Leu
740 745 750 cgc tat ccc atc aac gag gag gca ctg gag aag att ggc aca gct gag 2425
Arg Tyr Pro Ile Asn Glu Glu Ala Leu Glu Lys Ile Gly Thr Ala Glu
755 760 765 cct gac tac ggg gcc ctg tat gag gga cgc aac cct ggc ttc tat gta 2473
Pro Asp Tyr Gly Ala Leu Tyr Glu Gly Arg Asn Pro Gly Phe Tyr Val
770 775 780 gag gca aac cct atg cca act ttc aag tgt gca gtc aaa gcc ctc ttt 2521
Glu Ala Asn Pro Met Pro Thr Phe Lys Cys Ala Val Lys Ala Leu Phe
785 790 795 800 gac tac aag gcc cag agg gag gac gag ctg acc ttc atc aag agc gcc 2569
Asp Tyr Lys Ala Gln Arg Glu Asp Glu Leu Thr Phe Ile Lys Ser Ala
805 810 815 atc atc cag aat gtg gag aag caa gag gga ggc tgg tgg cga ggg gac 2617
Ile Ile Gln Asn Val Glu Lys Gln Glu Gly Gly Trp Trp Arg Gly Asp
820 825 830 tac gga ggg aag aag cag ctg tgg ttc cca tca aac tac gtg gaa gag 2665
Tyr Gly Gly Lys Lys Gln Leu Trp Phe Pro Ser Asn Tyr Val Glu Glu
835 840 845 atg gtc aac ccc gtg gcc ctg gag ccg gag agg gag cac ttg gac gag 2713
Met Val Asn Pro Val Ala Leu Glu Pro Glu Arg Glu His Leu Asp Glu
850 855 860 aac agc ccc cta ggg gac ttg ctg cgg ggg gtc ttg gat gtg ccg gct 2761
Asn Ser Pro Leu Gly Asp Leu Leu Arg Gly Val Leu Asp Val Pro Ala
865 870 875 880 tgt cag att gcc atc cgt cct gag ggc aag aac aac cgg ctc ttc gtc 2809
Cys Gln Ile Ala Ile Arg Pro Glu Gly Lys Asn Asn Arg Leu Phe Val
885 890 895 ttc tcc atc agc atg gcg tcg gtg gcc cac tgg tcc ctg gat gtt gct 2857
Phe Ser Ile Ser Met Ala Ser Val Ala His Trp Ser Leu Asp Val Ala
900 905 910 gcc gac tca cag gag gag ctg cag gac tgg gtg aaa aag atc cgt gaa 2905
Ala Asp Ser Gln Glu Glu Leu Gln Asp Trp Val Lys Lys Ile Arg Glu
915 920 925 gtg gcc cag aca gca gac gcc agg ctc act gaa ggg aag ata atg gaa 2953
Val Ala Gln Thr Ala Asp Ala Arg Leu Thr Glu Gly Lys Ile Met Glu
930 935 940 cgg agg aag aag att gcc ctg gag ctc tct gaa ctt gtc gtc tac tgc 3001
Arg Arg Lys Lys Ile Ala Leu Glu Leu Ser Glu Leu Val Val Tyr Cys
945 950 955 960 cgg cct gtt ccc ttt gat gaa gag aag att ggc aca gaa cgt gct tgc 3049
Arg Pro Val Pro Phe Asp Glu Glu Lys Ile Gly Thr Glu Arg Ala Cys
965 970 975 tac cgg gac atg tca tcc ttc ccg gaa acc aag gct gag aaa tac gtg 3097
Tyr Arg Asp Met Ser Ser Phe Pro Glu Thr Lys Ala Glu Lys Tyr Val
980 985 990 aac aag gcc aaa ggc aag aag ttc ctt cag tac aat cga ctg cag ctc 3145
Asn Lys Ala Lys Gly Lys Lys Phe Leu Gln Tyr Asn Arg Leu Gln Leu
995 1000 1005 tcc cgc atc tac ccc aag ggc cag cga ctg gat tcc tcc aac tac 3190
Ser Arg Ile Tyr Pro Lys Gly Gln Arg Leu Asp Ser Ser Asn Tyr
1010 1015 1020 gat cct ttg ccc atg tgg atc tgt ggc agt cag ctt gtg gcc ctc 3235
Asp Pro Leu Pro Met Trp Ile Cys Gly Ser Gln Leu Val Ala Leu
1025 1030 1035

-continued

```
aac ttc  cag acc cct gac aag  cct atg cag atg aac  cag gcc ctc      3280
Asn Phe  Gln Thr Pro Asp Lys  Pro Met Gln Met Asn  Gln Ala Leu
    1040                 1045                 1050

ttc atg  acg ggc agg cac tgt  ggc tac gtg ctg cag  cca agc acc      3325
Phe Met  Thr Gly Arg His Cys  Gly Tyr Val Leu Gln  Pro Ser Thr
    1055                 1060                 1065

atg cgg  gat gag gcc ttc gac  ccc ttt gac aag agc  agc ctc cgc      3370
Met Arg  Asp Glu Ala Phe Asp  Pro Phe Asp Lys Ser  Ser Leu Arg
    1070                 1075                 1080

ggg ctg  gag cca tgt gcc atc  tct att gag gtg ctg  ggg gcc cga      3415
Gly Leu  Glu Pro Cys Ala Ile  Ser Ile Glu Val Leu  Gly Ala Arg
    1085                 1090                 1095

cat ctg  cca aag aat ggc cga  ggc att gtg tgt cct  ttt gtg gag      3460
His Leu  Pro Lys Asn Gly Arg  Gly Ile Val Cys Pro  Phe Val Glu
    1100                 1105                 1110

att gag  gtg gct gga gct gag  tat gac agc acc aag  cag aag aca      3505
Ile Glu  Val Ala Gly Ala Glu  Tyr Asp Ser Thr Lys  Gln Lys Thr
    1115                 1120                 1125

gag ttt  gtg gtg gac aat gga  ctc aac cct gta tgg  cca gcc aag      3550
Glu Phe  Val Val Asp Asn Gly  Leu Asn Pro Val Trp  Pro Ala Lys
    1130                 1135                 1140

ccc ttc  cac ttc cag atc agt  aac cct gaa ttt gcc  ttt ctg cgc      3595
Pro Phe  His Phe Gln Ile Ser  Asn Pro Glu Phe Ala  Phe Leu Arg
    1145                 1150                 1155

ttc gtg  gtg tat gag gaa gac  atg ttt agt gac cag  aat ttc ctg      3640
Phe Val  Val Tyr Glu Glu Asp  Met Phe Ser Asp Gln  Asn Phe Leu
    1160                 1165                 1170

gct cag  gct act ttc cca gta  aaa ggc ctg aag aca  gga tac aga      3685
Ala Gln  Ala Thr Phe Pro Val  Lys Gly Leu Lys Thr  Gly Tyr Arg
    1175                 1180                 1185

gca gtg  cct ttg aag aac aac  tac agt gag gac ctg  gag ttg gcc      3730
Ala Val  Pro Leu Lys Asn Asn  Tyr Ser Glu Asp Leu  Glu Leu Ala
    1190                 1195                 1200

tcc ctg  ctg atc aag att gac  att ttc cct gcc aag  cag gag aat      3775
Ser Leu  Leu Ile Lys Ile Asp  Ile Phe Pro Ala Lys  Gln Glu Asn
    1205                 1210                 1215

ggt gac  ctc agt ccc ttc agt  ggt acg tcc ctg cgg  gag cgg ggc      3820
Gly Asp  Leu Ser Pro Phe Ser  Gly Thr Ser Leu Arg  Glu Arg Gly
    1220                 1225                 1230

tca gat  gcc tca ggc cag ctg  ttt cat ggc cga gcc  cgg gaa ggc      3865
Ser Asp  Ala Ser Gly Gln Leu  Phe His Gly Arg Ala  Arg Glu Gly
    1235                 1240                 1245

tcc ttt  gaa tcc cgc tac cag  cag ccg ttt gag gac  ttc cgc atc      3910
Ser Phe  Glu Ser Arg Tyr Gln  Gln Pro Phe Glu Asp  Phe Arg Ile
    1250                 1255                 1260

tcc cag  gag cat ctc gca gac  cat ttt gac agt cga  gaa cga agg      3955
Ser Gln  Glu His Leu Ala Asp  His Phe Asp Ser Arg  Glu Arg Arg
    1265                 1270                 1275

gcc cca  aga agg act cgg gtc  aat gga gac aac cgc  ctc tag          3997
Ala Pro  Arg Arg Thr Arg Val  Asn Gly Asp Asn Arg  Leu
    1280                 1285                 1290

ttgtacccca gcctcgttgg agagcagcag gtgctgtgcg ccttgtagaa tgccgcgaac   4057

tgggttcttt ggaagcagcc ccctgtggcg gccttccggg tctcgcagcc tgaagcctgg   4117

attccagcag tgaatgctag acagaaacca agccattaat gagatgttat tactgttttg   4177

ggcctccatg ccccagctct ggatgaaggc aaaaactgta ctgtgtttcg cattaagcac   4237

acacatctgg ccctgacttc tggagatgga tccttccatc ttgtggggcc aggaccatgg   4297

ccgaagcccc ttggagagag aggctgcctc agccagtggc acaggagact ccaaggagct   4357
```

-continued

```
actgacattc ctaagagtgg aggaggagga ggagccttgc tgggccaggg aaacaaagtt   4417

tacattgtcc tgtagcttta aaaccacagc tgggcagggt gagaagctag atgcccctgc   4477

agtttggccc tggagccagg gcagaggaat gtagggcctg catggagaag ggttctgccc   4537

tgcctgagga ggaggacaca gcacaagggc acattgccca tggctgggaa catgacccag   4597

cctgaaagat acaggggatc atgttaaaaa tagcagtatt atttttcgtc tcaatggtat   4657

tgtaactaag ttatttactc ctcctgctcc tcacccctgt agggaaacct tggagaggag   4717

agtggcaggt gggctgcctg ctgtgttaag aggacttagt ttgtgatgta aggcactgtc   4777

aggaatgggg ggcgggccag ggtgggaaga gaagaaatag cagagcctat tttggtgagg   4837

ttttttgttt ttaagtcaaa gaagactcag tatgctttcc ctgaggaatg aaaaagggat   4897

tgaggagttg cctgactcct gggtgggtgg ggtacaggca gttaggtgct gaatgaagct   4957

gccatccttg ctgcagcttc taactggtaa aaagatccag ggatggagat gggaaggtta   5017

gaaaggcagc cctcacctct gaggacagag gccggggtcc aggcccgtgg gcgcaaaggt   5077

gcctcatagc atagccagca ttcagcacac acaaacctac tgcccacatt tgggctcagg   5137

gttggccatt tgctagttct gctgccctct taagatctga ctgccaaata aatcatcctc   5197

atgtcctt                                                            5205


<210> SEQ ID NO 2
<211> LENGTH: 1291
<212> TYPE: PRT
<213> ORGANISM: Homo sapiens

<400> SEQUENCE: 2

Met Ala Gly Ala Ala Ser Pro Cys Ala Asn Gly Cys Gly Pro Gly Ala
1               5                   10                  15

Pro Ser Asp Ala Glu Val Leu His Leu Cys Arg Ser Leu Glu Val Gly
            20                  25                  30

Thr Val Met Thr Leu Phe Tyr Ser Lys Lys Ser Gln Arg Pro Glu Arg
        35                  40                  45

Lys Thr Phe Gln Val Lys Leu Glu Thr Arg Gln Ile Thr Trp Ser Arg
    50                  55                  60

Gly Ala Asp Lys Ile Glu Gly Ala Ile Asp Ile Arg Glu Ile Lys Glu
65                  70                  75                  80

Ile Arg Pro Gly Lys Thr Ser Arg Asp Phe Asp Arg Tyr Gln Glu Asp
                85                  90                  95

Pro Ala Phe Arg Pro Asp Gln Ser His Cys Phe Val Ile Leu Tyr Gly
            100                 105                 110

Met Glu Phe Arg Leu Lys Thr Leu Ser Leu Gln Ala Thr Ser Glu Asp
        115                 120                 125

Glu Val Asn Met Trp Ile Lys Gly Leu Thr Trp Leu Met Glu Asp Thr
    130                 135                 140

Leu Gln Ala Pro Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Leu Glu Gln Arg Ser Gly Asp Ile
        195                 200                 205

Thr Tyr Gly Gln Phe Ala Gln Leu Tyr Arg Ser Leu Met Tyr Ser Ala
```

-continued

```
    210                 215                 220

Gln Lys Thr Met Asp Leu Pro Phe Leu Glu Ala Ser Thr Leu Arg Ala
225                 230                 235                 240

Gly Glu Arg Pro Glu Leu Cys Arg Val Ser Leu Pro Glu Phe Gln Gln
                245                 250                 255

Phe Leu Leu Asp Tyr Gln Gly Glu Leu Trp Ala Val Asp Arg Leu Gln
            260                 265                 270

Val Gln Glu Phe Met Leu Ser Phe Leu Arg Asp Pro Leu Arg Glu Ile
        275                 280                 285

Glu Glu Pro Tyr Phe Phe Leu Asp Glu Phe Val Thr Phe Leu Phe Ser
    290                 295                 300

Lys Glu Asn Ser Val Trp Asn Ser Gln Leu Asp Ala Val Cys Pro Asp
305                 310                 315                 320

Thr Met Asn Asn Pro Leu Ser His Tyr Trp Ile Ser Ser Ser His Asn
                325                 330                 335

Thr Tyr Leu Thr Gly Asp Gln Phe Ser Ser Glu Ser Ser Leu Glu Ala
            340                 345                 350

Tyr Ala Arg Cys Leu Arg Met Gly Cys Arg Cys Ile Glu Leu Asp Cys
        355                 360                 365

Trp Asp Gly Pro Asp Gly Met Pro Val Ile Tyr His Gly His Thr Leu
    370                 375                 380

Thr Thr Lys Ile Lys Phe Ser Asp Val Leu His Thr Ile Lys Glu His
385                 390                 395                 400

Ala Phe Val Ala Ser Glu Tyr Pro Val Ile Leu Ser Ile Glu Asp His
                405                 410                 415

Cys Ser Ile Ala Gln Gln Arg Asn Met Ala Gln Tyr Phe Lys Lys Val
            420                 425                 430

Leu Gly Asp Thr Leu Leu Thr Lys Pro Val Glu Ile Ser Ala Asp Gly
        435                 440                 445

Leu Pro Ser Pro Asn Gln Leu Lys Arg Lys Ile Leu Ile Lys His Lys
    450                 455                 460

Lys Leu Ala Glu Gly Ser Ala Tyr Glu Glu Val Pro Thr Ser Met Met
465                 470                 475                 480

Tyr Ser Glu Asn Asp Ile Ser Asn Ser Ile Lys Asn Gly Ile Leu Tyr
                485                 490                 495

Leu Glu Asp Pro Val Asn His Glu Trp Tyr Pro His Tyr Phe Val Leu
            500                 505                 510

Thr Ser Ser Lys Ile Tyr Tyr Ser Glu Glu Thr Ser Ser Asp Gln Gly
        515                 520                 525

Asn Glu Asp Glu Glu Glu Pro Lys Glu Val Ser Ser Ser Thr Glu Leu
    530                 535                 540

His Ser Asn Glu Lys Trp Phe His Gly Lys Leu Gly Ala Gly Arg Asp
545                 550                 555                 560

Gly Arg His Ile Ala Glu Arg Leu Leu Thr Glu Tyr Cys Ile Glu Thr
                565                 570                 575

Gly Ala Pro Asp Gly Ser Phe Leu Val Arg Glu Ser Glu Thr Phe Val
            580                 585                 590

Gly Asp Tyr Thr Leu Ser Phe Trp Arg Asn Gly Lys Val Gln His Cys
        595                 600                 605

Arg Ile His Ser Arg Gln Asp Ala Gly Thr Pro Lys Phe Phe Leu Thr
    610                 615                 620

Asp Asn Leu Val Phe Asp Ser Leu Tyr Asp Leu Ile Thr His Tyr Gln
625                 630                 635                 640
```

-continued

```
Gln Val Pro Leu Arg Cys Asn Glu Phe Glu Met Arg Leu Ser Glu Pro
                645                 650                 655

Val Pro Gln Thr Asn Ala His Glu Ser Lys Glu Trp Tyr His Ala Ser
            660                 665                 670

Leu Thr Arg Ala Gln Ala Glu His Met Leu Met Arg Val Pro Arg Asp
        675                 680                 685

Gly Ala Phe Leu Val Arg Lys Arg Asn Glu Pro Asn Ser Tyr Ala Ile
    690                 695                 700

Ser Phe Arg Ala Glu Gly Lys Ile Lys His Cys Arg Val Gln Gln Glu
705                 710                 715                 720

Gly Gln Thr Val Met Leu Gly Asn Ser Glu Phe Asp Ser Leu Val Asp
                725                 730                 735

Leu Ile Ser Tyr Tyr Glu Lys His Pro Leu Tyr Arg Lys Met Lys Leu
            740                 745                 750

Arg Tyr Pro Ile Asn Glu Glu Ala Leu Glu Lys Ile Gly Thr Ala Glu
        755                 760                 765

Pro Asp Tyr Gly Ala Leu Tyr Glu Gly Arg Asn Pro Gly Phe Tyr Val
    770                 775                 780

Glu Ala Asn Pro Met Pro Thr Phe Lys Cys Ala Val Lys Ala Leu Phe
785                 790                 795                 800

Asp Tyr Lys Ala Gln Arg Glu Asp Glu Leu Thr Phe Ile Lys Ser Ala
                805                 810                 815

Ile Ile Gln Asn Val Glu Lys Gln Glu Gly Gly Trp Trp Arg Gly Asp
            820                 825                 830

Tyr Gly Gly Lys Lys Gln Leu Trp Phe Pro Ser Asn Tyr Val Glu Glu
        835                 840                 845

Met Val Asn Pro Val Ala Leu Glu Pro Glu Arg Glu His Leu Asp Glu
    850                 855                 860

Asn Ser Pro Leu Gly Asp Leu Leu Arg Gly Val Leu Asp Val Pro Ala
865                 870                 875                 880

Cys Gln Ile Ala Ile Arg Pro Glu Gly Lys Asn Asn Arg Leu Phe Val
                885                 890                 895

Phe Ser Ile Ser Met Ala Ser Val Ala His Trp Ser Leu Asp Val Ala
            900                 905                 910

Ala Asp Ser Gln Glu Glu Leu Gln Asp Trp Val Lys Lys Ile Arg Glu
        915                 920                 925

Val Ala Gln Thr Ala Asp Ala Arg Leu Thr Glu Gly Lys Ile Met Glu
    930                 935                 940

Arg Arg Lys Lys Ile Ala Leu Glu Leu Ser Glu Leu Val Val Tyr Cys
945                 950                 955                 960

Arg Pro Val Pro Phe Asp Glu Glu Lys Ile Gly Thr Glu Arg Ala Cys
                965                 970                 975

Tyr Arg Asp Met Ser Ser Phe Pro Glu Thr Lys Ala Glu Lys Tyr Val
            980                 985                 990

Asn Lys Ala Lys Gly Lys Lys Phe  Leu Gln Tyr Asn Arg  Leu Gln Leu
        995                 1000                1005

Ser Arg  Ile Tyr Pro Lys Gly  Gln Arg Leu Asp Ser  Ser Asn Tyr
    1010                1015                1020

Asp Pro  Leu Pro Met Trp Ile  Cys Gly Ser Gln Leu  Val Ala Leu
    1025                1030                1035

Asn Phe  Gln Thr Pro Asp Lys  Pro Met Gln Met Asn  Gln Ala Leu
    1040                1045                1050
```

-continued

Phe Met Thr Gly Arg His Cys Gly Tyr Val Leu Gln Pro Ser Thr
1055 1060 1065

Met Arg Asp Glu Ala Phe Asp Pro Phe Asp Lys Ser Ser Leu Arg
1070 1075 1080

Gly Leu Glu Pro Cys Ala Ile Ser Ile Glu Val Leu Gly Ala Arg
1085 1090 1095

His Leu Pro Lys Asn Gly Arg Gly Ile Val Cys Pro Phe Val Glu
1100 1105 1110

Ile Glu Val Ala Gly Ala Glu Tyr Asp Ser Thr Lys Gln Lys Thr
1115 1120 1125

Glu Phe Val Val Asp Asn Gly Leu Asn Pro Val Trp Pro Ala Lys
1130 1135 1140

Pro Phe His Phe Gln Ile Ser Asn Pro Glu Phe Ala Phe Leu Arg
1145 1150 1155

Phe Val Val Tyr Glu Glu Asp Met Phe Ser Asp Gln Asn Phe Leu
1160 1165 1170

Ala Gln Ala Thr Phe Pro Val Lys Gly Leu Lys Thr Gly Tyr Arg
1175 1180 1185

Ala Val Pro Leu Lys Asn Asn Tyr Ser Glu Asp Leu Glu Leu Ala
1190 1195 1200

Ser Leu Leu Ile Lys Ile Asp Ile Phe Pro Ala Lys Gln Glu Asn
1205 1210 1215

Gly Asp Leu Ser Pro Phe Ser Gly Thr Ser Leu Arg Glu Arg Gly
1220 1225 1230

Ser Asp Ala Ser Gly Gln Leu Phe His Gly Arg Ala Arg Glu Gly
1235 1240 1245

Ser Phe Glu Ser Arg Tyr Gln Gln Pro Phe Glu Asp Phe Arg Ile
1250 1255 1260

Ser Gln Glu His Leu Ala Asp His Phe Asp Ser Arg Glu Arg Arg
1265 1270 1275

Ala Pro Arg Arg Thr Arg Val Asn Gly Asp Asn Arg Leu
1280 1285 1290

<210> SEQ ID NO 3
<211> LENGTH: 4242
<212> TYPE: DNA
<213> ORGANISM: Homo sapiens
<220> FEATURE:
<221> NAME/KEY: CDS
<222> LOCATION: (153)..(3911)

<400> SEQUENCE: 3
gaattcggcg ctgagtgacc cgagtcggga cgcgggctgc gcgcgcggga ccccggagcc 60
caaacccggg gcaggcgggc agctgtgccc gggcggcacg gccagcttcc tgatttctcc 120
cgattccttc cttctccctg gagcggccga ca atg tcc acc acg gtc aat gta 173
Met Ser Thr Thr Val Asn Val
1 5 gat tcc ctt gcg gaa tat gag aag agc cag atc aag aga gcc ctg gag 221
Asp Ser Leu Ala Glu Tyr Glu Lys Ser Gln Ile Lys Arg Ala Leu Glu
10 15 20 ctg ggg acg gtg atg act gtg ttc agc ttc cgc aag tcc acc ccc gag 269
Leu Gly Thr Val Met Thr Val Phe Ser Phe Arg Lys Ser Thr Pro Glu
25 30 35 cgg aga acc gtc cag gtg atc atg gag acg cgg cag gtg gcc tgg agc 317
Arg Arg Thr Val Gln Val Ile Met Glu Thr Arg Gln Val Ala Trp Ser
40 45 50 55

-continued

```
aag acc gcc gac aag atc gag ggc ttc ttg gat atc atg gaa ata aaa      365
Lys Thr Ala Asp Lys Ile Glu Gly Phe Leu Asp Ile Met Glu Ile Lys
                60                  65                  70

gaa atc cgc cca ggg aag aac tcc aaa gat ttc gag cga gca aaa gca      413
Glu Ile Arg Pro Gly Lys Asn Ser Lys Asp Phe Glu Arg Ala Lys Ala
            75                  80                  85

gtt cgc cag aaa gaa gac tgc tgc ttc acc atc cta tat ggc act cag      461
Val Arg Gln Lys Glu Asp Cys Cys Phe Thr Ile Leu Tyr Gly Thr Gln
        90                  95                  100

ttc gtc ctc agc acg ctc agc ttg gca gct gac tct aaa gag gat gca      509
Phe Val Leu Ser Thr Leu Ser Leu Ala Ala Asp Ser Lys Glu Asp Ala
    105                 110                 115

gtt aac tgg ctc tct ggc ttg aaa atc tta cac cag gaa gcg atg aat      557
Val Asn Trp Leu Ser Gly Leu Lys Ile Leu His Gln Glu Ala Met Asn
120                 125                 130                 135

gcg tcc acg ccc acc att atc gag agt tgg ctg aga aag cag ata tat      605
Ala Ser Thr Pro Thr Ile Ile Glu Ser Trp Leu Arg Lys Gln Ile Tyr
                140                 145                 150

tct gtg gat caa acc aga aga aac agc atc agt ctc cga gag ttg aag      653
Ser Val Asp Gln Thr Arg Arg Asn Ser Ile Ser Leu Arg Glu Leu Lys
            155                 160                 165

acc atc ttg ccc ctg atc aac ttt aaa gtg agc agt gcc aag ttc ctt      701
Thr Ile Leu Pro Leu Ile Asn Phe Lys Val Ser Ser Ala Lys Phe Leu
        170                 175                 180

aaa gat aag ttt gtg gaa ata gga gca cac aaa gat gag ctc agc ttt      749
Lys Asp Lys Phe Val Glu Ile Gly Ala His Lys Asp Glu Leu Ser Phe
    185                 190                 195

gaa cag ttc cat ctc ttc tat aaa aaa ctt atg ttt gaa cag caa aaa      797
Glu Gln Phe His Leu Phe Tyr Lys Lys Leu Met Phe Glu Gln Gln Lys
200                 205                 210                 215

tcg att ctc gat gaa ttc aaa aag gat tcg tcc gtg ttc atc ctg ggg      845
Ser Ile Leu Asp Glu Phe Lys Lys Asp Ser Ser Val Phe Ile Leu Gly
                220                 225                 230

aac act gac agg ccg gat gcc tct gct gtt tac ctg cat gac ttc cag      893
Asn Thr Asp Arg Pro Asp Ala Ser Ala Val Tyr Leu His Asp Phe Gln
            235                 240                 245

agg ttt ctc ata cat gaa cag cag gag cat tgg gct cag gat ctg aac      941
Arg Phe Leu Ile His Glu Gln Gln Glu His Trp Ala Gln Asp Leu Asn
        250                 255                 260

aaa gtc cgt gag cgg atg aca aag ttc att gat gac acc atg cgt gaa      989
Lys Val Arg Glu Arg Met Thr Lys Phe Ile Asp Asp Thr Met Arg Glu
    265                 270                 275

act gct gag cct ttc ttg ttt gtg gat gag ttc ctc acg tac ctg ttt     1037
Thr Ala Glu Pro Phe Leu Phe Val Asp Glu Phe Leu Thr Tyr Leu Phe
280                 285                 290                 295

tca cga gaa aac agc atc tgg gat gag aag tat gac gcg gtg gac atg     1085
Ser Arg Glu Asn Ser Ile Trp Asp Glu Lys Tyr Asp Ala Val Asp Met
                300                 305                 310

cag gac atg aac aac ccc ctg tct cat tac tgg atc tcc tcg tca cat     1133
Gln Asp Met Asn Asn Pro Leu Ser His Tyr Trp Ile Ser Ser Ser His
            315                 320                 325

aac acg tac ctt aca ggt gac cag ctg cgg agc gag tcg tcc cca gaa     1181
Asn Thr Tyr Leu Thr Gly Asp Gln Leu Arg Ser Glu Ser Ser Pro Glu
        330                 335                 340

gct tac atc cgc tgc ctg cgc atg ggc tgt cgc tgc att gaa ctg gac     1229
Ala Tyr Ile Arg Cys Leu Arg Met Gly Cys Arg Cys Ile Glu Leu Asp
    345                 350                 355

tgc tgg gac ggg ccc gat ggg aag ccg gtc atc tac cat ggc tgg acg     1277
Cys Trp Asp Gly Pro Asp Gly Lys Pro Val Ile Tyr His Gly Trp Thr
360                 365                 370                 375
```

-continued

```
cgg act acc aag atc aag ttt gat gac gtc gtg cag gcc atc aaa gac      1325
Arg Thr Thr Lys Ile Lys Phe Asp Asp Val Val Gln Ala Ile Lys Asp
                380                 385                 390

cac gcc ttt gtt acc tcg agc ttc cca gtg atc ctg tcc atc gag gag      1373
His Ala Phe Val Thr Ser Ser Phe Pro Val Ile Leu Ser Ile Glu Glu
            395                 400                 405

cac tgc agc gtg gag caa cag cgt cac atg gcc aag gcc ttc aag gaa      1421
His Cys Ser Val Glu Gln Gln Arg His Met Ala Lys Ala Phe Lys Glu
        410                 415                 420

gta ttt ggc gac ctg ctg ttg acg aag ccc acg gag gcc agt gct gac      1469
Val Phe Gly Asp Leu Leu Leu Thr Lys Pro Thr Glu Ala Ser Ala Asp
    425                 430                 435

cag ctg ccc tcg ccc agc cag ctg cgg gag aag atc atc atc aag cat      1517
Gln Leu Pro Ser Pro Ser Gln Leu Arg Glu Lys Ile Ile Ile Lys His
440                 445                 450                 455

aag aag ctg ggc ccc cga ggc gat gtg gat gtc aac atg gag gac aag      1565
Lys Lys Leu Gly Pro Arg Gly Asp Val Asp Val Asn Met Glu Asp Lys
                460                 465                 470

aag gac gaa cac aag caa cag ggg gag ctg tac atg tgg gat tcc att      1613
Lys Asp Glu His Lys Gln Gln Gly Glu Leu Tyr Met Trp Asp Ser Ile
            475                 480                 485

gac cag aaa tgg act cgg cac tac tgc gcc att gct gat gcc aag ctg      1661
Asp Gln Lys Trp Thr Arg His Tyr Cys Ala Ile Ala Asp Ala Lys Leu
        490                 495                 500

tcc ttc agt gat gac att gaa cag act atg gag gag gaa gtg ccc cag      1709
Ser Phe Ser Asp Asp Ile Glu Gln Thr Met Glu Glu Glu Val Pro Gln
    505                 510                 515

gat ata ccc cct aca gaa cta cat ttt ggg gag aaa tgg ttc cac aag      1757
Asp Ile Pro Pro Thr Glu Leu His Phe Gly Glu Lys Trp Phe His Lys
520                 525                 530                 535

aag gtg gag aag agg acg agt gcc gag aag ttg ctg cag gaa tac tgc      1805
Lys Val Glu Lys Arg Thr Ser Ala Glu Lys Leu Leu Gln Glu Tyr Cys
                540                 545                 550

atg gag acg ggg ggc aag gat ggc acc ttc ctg gtt cgg gag agc gag      1853
Met Glu Thr Gly Gly Lys Asp Gly Thr Phe Leu Val Arg Glu Ser Glu
            555                 560                 565

acc ttc ccc aat gac tac acc ctg tcc ttc tgg cgg tca ggc cgg gtc      1901
Thr Phe Pro Asn Asp Tyr Thr Leu Ser Phe Trp Arg Ser Gly Arg Val
        570                 575                 580

cag cac tgc cgg atc cgc tcc acc atg gag ggc ggg acc ctg aaa tac      1949
Gln His Cys Arg Ile Arg Ser Thr Met Glu Gly Gly Thr Leu Lys Tyr
    585                 590                 595

tac ttg act gac aac ctg agg ttc agg agg atg tat gcc ctc atc cag      1997
Tyr Leu Thr Asp Asn Leu Arg Phe Arg Arg Met Tyr Ala Leu Ile Gln
600                 605                 610                 615

cac tac cgc gag acg cac ctg ccg tgc gcc gag ttc gag ctg cgg ctc      2045
His Tyr Arg Glu Thr His Leu Pro Cys Ala Glu Phe Glu Leu Arg Leu
                620                 625                 630

acg gac cct gtg ccc aac ccc aac ccc cac gag tcc aag ccg tgg tac      2093
Thr Asp Pro Val Pro Asn Pro Asn Pro His Glu Ser Lys Pro Trp Tyr
            635                 640                 645

tat gac agc ctg agc cgc gga gag gca gag gac atg ctg atg agg att      2141
Tyr Asp Ser Leu Ser Arg Gly Glu Ala Glu Asp Met Leu Met Arg Ile
        650                 655                 660

ccc cgg gac ggg gcc ttc ctg atc cgg aag cga gag ggg agc gac tcc      2189
Pro Arg Asp Gly Ala Phe Leu Ile Arg Lys Arg Glu Gly Ser Asp Ser
    665                 670                 675

tat gcc atc acc ttc agg gct agg ggc aag gta aag cat tgt cgc atc      2237
Tyr Ala Ile Thr Phe Arg Ala Arg Gly Lys Val Lys His Cys Arg Ile
```

-continued

```
680                 685                 690                 695

aac cgg gac ggc cgg cac ttt gtg ctg ggg acc tcc gcc tat ttt gag      2285
Asn Arg Asp Gly Arg His Phe Val Leu Gly Thr Ser Ala Tyr Phe Glu
                700                 705                 710

agt ctg gtg gag ctc gtc agt tac tac gag aag cat tca ctc tac cga      2333
Ser Leu Val Glu Leu Val Ser Tyr Tyr Glu Lys His Ser Leu Tyr Arg
            715                 720                 725

aag atg aga ctg cgc tac ccc gtg acc ccc gag ctc ctg gag cgc tac      2381
Lys Met Arg Leu Arg Tyr Pro Val Thr Pro Glu Leu Leu Glu Arg Tyr
        730                 735                 740

aat acg gaa aga gat ata aac tcc ctc tac gac gtc agc aga atg tat      2429
Asn Thr Glu Arg Asp Ile Asn Ser Leu Tyr Asp Val Ser Arg Met Tyr
    745                 750                 755

gtg gat ccc agt gaa atc aat ccg tcc atg cct cag aga acc gtg aaa      2477
Val Asp Pro Ser Glu Ile Asn Pro Ser Met Pro Gln Arg Thr Val Lys
760                 765                 770                 775

gct ctg tat gac tac aaa gcc aag cga agc gat gag ctg agc ttc tgc      2525
Ala Leu Tyr Asp Tyr Lys Ala Lys Arg Ser Asp Glu Leu Ser Phe Cys
                780                 785                 790

cgt ggt gcc ctc atc cac aat gtc tcc aag gag ccc ggg ggc tgg tgg      2573
Arg Gly Ala Leu Ile His Asn Val Ser Lys Glu Pro Gly Gly Trp Trp
            795                 800                 805

aaa gga gac tat gga acc agg atc cag cag tac ttc cca tcc aac tac      2621
Lys Gly Asp Tyr Gly Thr Arg Ile Gln Gln Tyr Phe Pro Ser Asn Tyr
        810                 815                 820

gtc gag gac atc tca act gca gac ttc gag gag cta gaa aag cag att      2669
Val Glu Asp Ile Ser Thr Ala Asp Phe Glu Glu Leu Glu Lys Gln Ile
    825                 830                 835

att gaa gac aat ccc tta ggg tct ctt tgc aga gga ata ttg gac ctc      2717
Ile Glu Asp Asn Pro Leu Gly Ser Leu Cys Arg Gly Ile Leu Asp Leu
840                 845                 850                 855

aat acc tat aac gtc gtg aaa gcc cct cag gga aaa aac cag aag tcc      2765
Asn Thr Tyr Asn Val Val Lys Ala Pro Gln Gly Lys Asn Gln Lys Ser
                860                 865                 870

ttt gtc ttc atc ctg gag ccc aag gag cag ggc gat cct ccg gtg gag      2813
Phe Val Phe Ile Leu Glu Pro Lys Glu Gln Gly Asp Pro Pro Val Glu
            875                 880                 885

ttt gcc aca gac agg gtg gag gag ctc ttt gag tgg ttt cag agc atc      2861
Phe Ala Thr Asp Arg Val Glu Glu Leu Phe Glu Trp Phe Gln Ser Ile
        890                 895                 900

cga gag atc acg tgg aag att gac agc aag gag aac aac atg aag tac      2909
Arg Glu Ile Thr Trp Lys Ile Asp Ser Lys Glu Asn Asn Met Lys Tyr
    905                 910                 915

tgg gag aag aac cag tcc atc gcc atc gag ctc tct gac ctg gtt gtc      2957
Trp Glu Lys Asn Gln Ser Ile Ala Ile Glu Leu Ser Asp Leu Val Val
920                 925                 930                 935

tac tgc aaa cca acc agc aaa acc aag gac aac tta gaa aat cct gac      3005
Tyr Cys Lys Pro Thr Ser Lys Thr Lys Asp Asn Leu Glu Asn Pro Asp
                940                 945                 950

ttc cga gaa atc cgc tcc ttt gtg gag acg aag gct gac agc atc atc      3053
Phe Arg Glu Ile Arg Ser Phe Val Glu Thr Lys Ala Asp Ser Ile Ile
            955                 960                 965

aga cag aag ccc gtc gac ctc ctg aag tac aat caa aag ggc ctg acc      3101
Arg Gln Lys Pro Val Asp Leu Leu Lys Tyr Asn Gln Lys Gly Leu Thr
        970                 975                 980

cgc gtc tac cca aag gga caa aga gtt gac tct tca aac tac gac ccc      3149
Arg Val Tyr Pro Lys Gly Gln Arg Val Asp Ser Ser Asn Tyr Asp Pro
    985                 990                 995

ttc  cgc ctc tgg ctg tgc  ggt tct cag atg gtg  gca ctc aat ttc      3194
```

-continued

```
Phe  Arg Leu Trp Leu Cys  Gly Ser Gln Met Val  Ala Leu Asn Phe
1000                 1005                 1010

cag  acg gca gat aag tac  atg cag atg aat cac  gca ttg ttt tct      3239
Gln  Thr Ala Asp Lys Tyr  Met Gln Met Asn His  Ala Leu Phe Ser
1015                 1020                 1025

ctc  aac ggg cgc acg ggc  tac gtt ctg cag cct  gag agc atg agg      3284
Leu  Asn Gly Arg Thr Gly  Tyr Val Leu Gln Pro  Glu Ser Met Arg
1030                 1035                 1040

aca  gag aaa tat gac ccg  atg cca ccc gag tcc  cag agg aag atc      3329
Thr  Glu Lys Tyr Asp Pro  Met Pro Pro Glu Ser  Gln Arg Lys Ile
1045                 1050                 1055

ctg  atg acg ctg aca gtc  aag gtt ctc ggt gct  cgc cat ctc ccc      3374
Leu  Met Thr Leu Thr Val  Lys Val Leu Gly Ala  Arg His Leu Pro
1060                 1065                 1070

aaa  ctt gga cga agt att  gcc tgt ccc ttt gta  gaa gtg gag atc      3419
Lys  Leu Gly Arg Ser Ile  Ala Cys Pro Phe Val  Glu Val Glu Ile
1075                 1080                 1085

tgt  gga gcc gag tat ggc  aac aac aag ttc aag  acg acg gtt gtg      3464
Cys  Gly Ala Glu Tyr Gly  Asn Asn Lys Phe Lys  Thr Thr Val Val
1090                 1095                 1100

aat  gat aat ggc ctc agc  cct atc tgg gct cca  aca cag gag aag      3509
Asn  Asp Asn Gly Leu Ser  Pro Ile Trp Ala Pro  Thr Gln Glu Lys
1105                 1110                 1115

gtg  aca ttt gaa att tat  gac cca aac ctg gca  ttt ctg cgc ttt      3554
Val  Thr Phe Glu Ile Tyr  Asp Pro Asn Leu Ala  Phe Leu Arg Phe
1120                 1125                 1130

gtg  gtt tat gaa gaa gat  atg ttc agc gat ccc  aac ttt ctt gct      3599
Val  Val Tyr Glu Glu Asp  Met Phe Ser Asp Pro  Asn Phe Leu Ala
1135                 1140                 1145

cat  gcc act tac ccc att  aaa gca gtc aaa tca  gga ttc agg tcc      3644
His  Ala Thr Tyr Pro Ile  Lys Ala Val Lys Ser  Gly Phe Arg Ser
1150                 1155                 1160

gtt  cct ctg aag aat ggg  tac agc gag gac ata  gag ctg gct tcc      3689
Val  Pro Leu Lys Asn Gly  Tyr Ser Glu Asp Ile  Glu Leu Ala Ser
1165                 1170                 1175

ctc  ctg gtt ttc tgt gag  atg cgg cca gtc ctg  gag agc gaa gag      3734
Leu  Leu Val Phe Cys Glu  Met Arg Pro Val Leu  Glu Ser Glu Glu
1180                 1185                 1190

gaa  ctt tac tcc tcc tgt  cgc cag ctg agg agg  cgg caa gaa gaa      3779
Glu  Leu Tyr Ser Ser Cys  Arg Gln Leu Arg Arg  Arg Gln Glu Glu
1195                 1200                 1205

ctg  aac aac cag ctc ttt  ctg tat gac aca cac  cag aac ttg cgc      3824
Leu  Asn Asn Gln Leu Phe  Leu Tyr Asp Thr His  Gln Asn Leu Arg
1210                 1215                 1220

aat  gcc aac cgg gat gcc  ctg gtt aaa gag ttc  agt gtt aat gag      3869
Asn  Ala Asn Arg Asp Ala  Leu Val Lys Glu Phe  Ser Val Asn Glu
1225                 1230                 1235

aac  cac tcc agc tgt acc  agg aga aat gca aca  aga ggt taa          3911
Asn  His Ser Ser Cys Thr  Arg Arg Asn Ala Thr  Arg Gly
1240                 1245                 1250

gagagaagag agtcagcaac agcaagtttt actcatagaa gctggggtat gtgtgtaagg   3971

gtattgtgtg tgtgcgcatg tgtgtttgca tgtaggagaa cgtgccctat tcacactctg   4031

ggaagacgct aatctgtgac atcttttctt caagcctgcc atcaaggaca tttcttaaga   4091

cccaactggc atgagttggg gtaatttcct attattttca tcttggacaa cttctaactt   4151

atatctttat agaggattcc ccaaaatgtg ctcctcattt ttggcctctc atgttccaaa   4211

cctcattgaa taaaaagcaa tgaaaacctt g                                  4242
```

-continued

<210> SEQ ID NO 4
<211> LENGTH: 1252
<212> TYPE: PRT
<213> ORGANISM: Homo sapiens

<400> SEQUENCE: 4

```
Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
            20                  25                  30

Phe Arg Lys Ser Thr Pro Glu Arg Arg Thr Val Gln Val Ile Met Glu
        35                  40                  45

Thr Arg Gln Val Ala Trp Ser Lys Thr Ala Asp Lys Ile Glu Gly Phe
    50                  55                  60

Leu Asp Ile Met Glu Ile Lys Glu Ile Arg Pro Gly Lys Asn Ser Lys
65                  70                  75                  80

Asp Phe Glu Arg Ala Lys Ala Val Arg Gln Lys Glu Asp Cys Cys Phe
                85                  90                  95

Thr Ile Leu Tyr Gly Thr Gln Phe Val Leu Ser Thr Leu Ser Leu Ala
            100                 105                 110

Ala Asp Ser Lys Glu Asp Ala Val Asn Trp Leu Ser Gly Leu Lys Ile
        115                 120                 125

Leu His Gln Glu Ala Met Asn Ala Ser Thr Pro Thr Ile Ile Glu Ser
    130                 135                 140

Trp Leu Arg Lys Gln Ile Tyr Ser Val Asp Gln Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala
            180                 185                 190

His Lys Asp Glu Leu Ser Phe Glu Gln Phe His Leu Phe Tyr Lys Lys
        195                 200                 205

Leu Met Phe Glu Gln Gln Lys Ser Ile Leu Asp Glu Phe Lys Lys Asp
    210                 215                 220

Ser Ser Val Phe Ile Leu Gly Asn Thr Asp Arg Pro Asp Ala Ser Ala
225                 230                 235                 240

Val Tyr Leu His Asp Phe Gln Arg Phe Leu Ile His Glu Gln Gln Glu
                245                 250                 255

His Trp Ala Gln Asp Leu Asn Lys Val Arg Glu Arg Met Thr Lys Phe
            260                 265                 270

Ile Asp Asp Thr Met Arg Glu Thr Ala Glu Pro Phe Leu Phe Val Asp
        275                 280                 285

Glu Phe Leu Thr Tyr Leu Phe Ser Arg Glu Asn Ser Ile Trp Asp Glu
    290                 295                 300

Lys Tyr Asp Ala Val Asp Met Gln Asp Met Asn Asn Pro Leu Ser His
305                 310                 315                 320

Tyr Trp Ile Ser Ser Ser His Asn Thr Tyr Leu Thr Gly Asp Gln Leu
                325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
        355                 360                 365

Val Ile Tyr His Gly Trp Thr Arg Thr Thr Lys Ile Lys Phe Asp Asp
    370                 375                 380
```

-continued

```
Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
            420                 425                 430

Pro Thr Glu Ala Ser Ala Asp Gln Leu Pro Ser Pro Ser Gln Leu Arg
        435                 440                 445

Glu Lys Ile Ile Ile Lys His Lys Lys Leu Gly Pro Arg Gly Asp Val
    450                 455                 460

Asp Val Asn Met Glu Asp Lys Lys Asp Glu His Lys Gln Gln Gly Glu
465                 470                 475                 480

Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Asp Ile Glu Gln Thr
            500                 505                 510

Met Glu Glu Glu Val Pro Gln Asp Ile Pro Pro Thr Glu Leu His Phe
        515                 520                 525

Gly Glu Lys Trp Phe His Lys Lys Val Glu Lys Arg Thr Ser Ala Glu
    530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
            580                 585                 590

Glu Gly Gly Thr Leu Lys Tyr Tyr Leu Thr Asp Asn Leu Arg Phe Arg
        595                 600                 605

Arg Met Tyr Ala Leu Ile Gln His Tyr Arg Glu Thr His Leu Pro Cys
    610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Arg Asp Gly Ala Phe Leu Ile Arg
            660                 665                 670

Lys Arg Glu Gly Ser Asp Ser Tyr Ala Ile Thr Phe Arg Ala Arg Gly
        675                 680                 685

Lys Val Lys His Cys Arg Ile Asn Arg Asp Gly Arg His Phe Val Leu
    690                 695                 700

Gly Thr Ser Ala Tyr Phe Glu Ser Leu Val Glu Leu Val Ser Tyr Tyr
705                 710                 715                 720

Glu Lys His Ser Leu Tyr Arg Lys Met Arg Leu Arg Tyr Pro Val Thr
                725                 730                 735

Pro Glu Leu Leu Glu Arg Tyr Asn Thr Glu Arg Asp Ile Asn Ser Leu
            740                 745                 750

Tyr Asp Val Ser Arg Met Tyr Val Asp Pro Ser Glu Ile Asn Pro Ser
        755                 760                 765

Met Pro Gln Arg Thr Val Lys Ala Leu Tyr Asp Tyr Lys Ala Lys Arg
    770                 775                 780

Ser Asp Glu Leu Ser Phe Cys Arg Gly Ala Leu Ile His Asn Val Ser
785                 790                 795                 800
```

-continued

```
Lys Glu Pro Gly Gly Trp Trp Lys Gly Asp Tyr Gly Thr Arg Ile Gln
                805                 810                 815

Gln Tyr Phe Pro Ser Asn Tyr Val Glu Asp Ile Ser Thr Ala Asp Phe
            820                 825                 830

Glu Glu Leu Glu Lys Gln Ile Ile Glu Asp Asn Pro Leu Gly Ser Leu
        835                 840                 845

Cys Arg Gly Ile Leu Asp Leu Asn Thr Tyr Asn Val Val Lys Ala Pro
    850                 855                 860

Gln Gly Lys Asn Gln Lys Ser Phe Val Phe Ile Leu Glu Pro Lys Glu
865                 870                 875                 880

Gln Gly Asp Pro Pro Val Glu Phe Ala Thr Asp Arg Val Glu Glu Leu
                885                 890                 895

Phe Glu Trp Phe Gln Ser Ile Arg Glu Ile Thr Trp Lys Ile Asp Ser
            900                 905                 910

Lys Glu Asn Asn Met Lys Tyr Trp Glu Lys Asn Gln Ser Ile Ala Ile
        915                 920                 925

Glu Leu Ser Asp Leu Val Val Tyr Cys Lys Pro Thr Ser Lys Thr Lys
    930                 935                 940

Asp Asn Leu Glu Asn Pro Asp Phe Arg Glu Ile Arg Ser Phe Val Glu
945                 950                 955                 960

Thr Lys Ala Asp Ser Ile Ile Arg Gln Lys Pro Val Asp Leu Leu Lys
                965                 970                 975

Tyr Asn Gln Lys Gly Leu Thr Arg Val Tyr Pro Lys Gly Gln Arg Val
            980                 985                 990

Asp Ser Ser Asn Tyr Asp Pro Phe  Arg Leu Trp Leu Cys  Gly Ser Gln
        995                 1000                1005

Met Val  Ala Leu Asn Phe Gln  Thr Ala Asp Lys Tyr  Met Gln Met
    1010                 1015                 1020

Asn His  Ala Leu Phe Ser Leu  Asn Gly Arg Thr Gly  Tyr Val Leu
    1025                 1030                 1035

Gln Pro  Glu Ser Met Arg Thr  Glu Lys Tyr Asp Pro  Met Pro Pro
    1040                 1045                 1050

Glu Ser  Gln Arg Lys Ile Leu  Met Thr Leu Thr Val  Lys Val Leu
    1055                 1060                 1065

Gly Ala  Arg His Leu Pro Lys  Leu Gly Arg Ser Ile  Ala Cys Pro
    1070                 1075                 1080

Phe Val  Glu Val Glu Ile Cys  Gly Ala Glu Tyr Gly  Asn Asn Lys
    1085                 1090                 1095

Phe Lys  Thr Thr Val Val Asn  Asp Asn Gly Leu Ser  Pro Ile Trp
    1100                 1105                 1110

Ala Pro  Thr Gln Glu Lys Val  Thr Phe Glu Ile Tyr  Asp Pro Asn
    1115                 1120                 1125

Leu Ala  Phe Leu Arg Phe Val  Val Tyr Glu Glu Asp  Met Phe Ser
    1130                 1135                 1140

Asp Pro  Asn Phe Leu Ala His  Ala Thr Tyr Pro Ile  Lys Ala Val
    1145                 1150                 1155

Lys Ser  Gly Phe Arg Ser Val  Pro Leu Lys Asn Gly  Tyr Ser Glu
    1160                 1165                 1170

Asp Ile  Glu Leu Ala Ser Leu  Leu Val Phe Cys Glu  Met Arg Pro
    1175                 1180                 1185

Val Leu  Glu Ser Glu Glu Glu  Leu Tyr Ser Ser Cys  Arg Gln Leu
    1190                 1195                 1200

Arg Arg  Arg Gln Glu Glu Leu  Asn Asn Gln Leu Phe  Leu Tyr Asp
```

-continued

```
    1205                1210                1215

Thr His  Gln Asn Leu Arg Asn  Ala Asn Arg Asp Ala  Leu Val Lys
    1220                1225                1230

Glu Phe  Ser Val Asn Glu Asn  His Ser Ser Cys Thr  Arg Arg Asn
    1235                1240                1245

Ala Thr  Arg Gly
    1250
```